US010512478B2

(12) United States Patent
Greenhalgh et al.

(10) Patent No.: US 10,512,478 B2
(45) Date of Patent: Dec. 24, 2019

(54) CLOT-ENGULFING MECHANICAL THROMBECTOMY APPARATUSES

(71) Applicant: STRYKER CORPORATION, Fremont, CA (US)

(72) Inventors: E. Skott Greenhalgh, Gladwyne, PA (US); Michael P. Wallace, Pleasanton, CA (US)

(73) Assignee: Stryker Corporation, Fremont, CA (US)

( * ) Notice: Subject to any disclaimer, the term of this patent is extended or adjusted under 35 U.S.C. 154(b) by 274 days.

(21) Appl. No.: 15/497,092

(22) Filed: Apr. 25, 2017

(65) Prior Publication Data

US 2017/0303947 A1    Oct. 26, 2017

Related U.S. Application Data

(60) Provisional application No. 62/357,677, filed on Jul. 1, 2016, provisional application No. 62/345,152, filed
(Continued)

(51) Int. Cl.
*A61M 29/00* (2006.01)
*A61B 17/221* (2006.01)
(Continued)

(52) U.S. Cl.
CPC ...... *A61B 17/221* (2013.01); *A61B 17/22012* (2013.01); *A61B 17/22031* (2013.01); *A61B 17/22032* (2013.01); *A61M 25/0119* (2013.01); *A61M 39/06* (2013.01); *A61B 2017/00349* (2013.01); *A61B 2017/00367* (2013.01);
(Continued)

(58) Field of Classification Search
CPC ...... A61F 2/01; A61F 2/013; A61F 2002/011; A61B 17/221; A61B 17/22012; A61B 17/22031; A61B 17/22032; A61B 17/22034; A61B 17/22035;
(Continued)

(56) References Cited

U.S. PATENT DOCUMENTS 4,222,380 A    9/1980  Terayama
4,243,040 A    1/1981  Beecher
(Continued)

FOREIGN PATENT DOCUMENTS

AU    2015210338    8/2015
GB    1588072       4/1981
(Continued)

OTHER PUBLICATIONS

Notice of Allowance dated Mar. 22, 2018 for U.S. Appl. No. 15/496,668.
(Continued)

*Primary Examiner* — Melanie R Tyson
(74) *Attorney, Agent, or Firm* — Vista IP Law Group LLP

(57) ABSTRACT

Mechanical thrombectomy systems including an elongate catheter configured as an elongate inversion support, a flexible tractor configured to roll and invert over the distal end of the elongate inversion support, and a clot engaging member on the distal end of an elongate manipulator are described herein. These systems may capture a clot using the clot engaging member and draw the clot and clot engaging member and roll the flexible tractor into the catheter to remove the clot and clot engaging member from a vessel.

17 Claims, 14 Drawing Sheets

Related U.S. Application Data on Jun. 3, 2016, provisional application No. 62/327,024, filed on Apr. 25, 2016.

(51) Int. Cl.
*A61M 39/06* (2006.01)
*A61M 25/01* (2006.01)
*A61B 17/22* (2006.01)
*A61B 17/00* (2006.01)
*A61B 17/34* (2006.01)
*A61B 90/00* (2016.01)

(52) U.S. Cl.
CPC ............ *A61B 2017/00831* (2013.01); *A61B 2017/2215* (2013.01); *A61B 2017/22038* (2013.01); *A61B 2017/22079* (2013.01); *A61B 2017/3435* (2013.01); *A61B 2090/037* (2016.02); *A61M 2039/062* (2013.01)

(58) Field of Classification Search
CPC ........ A61B 17/22038; A61B 17/22079; A61B 17/2215; A61B 17/3435; A61M 25/0119
See application file for complete search history.

(56) References Cited

U.S. PATENT DOCUMENTS

| | | |
|---|---|---|
| 4,324,262 A | 4/1982 | Hall |
| 4,469,100 A | 9/1984 | Hardwick |
| 4,604,094 A | 8/1986 | Shook |
| 4,646,736 A | 3/1987 | Auth |
| 4,863,440 A | 9/1989 | Chin |
| 4,946,440 A | 8/1990 | Hall |
| 5,364,345 A | 11/1994 | Lowery et al. |
| 5,389,100 A | 2/1995 | Bacich et al. |
| 5,662,703 A | 9/1997 | Yurek et al. |
| 5,971,938 A | 10/1999 | Hart et al. |
| 6,221,006 B1 | 4/2001 | Dubrul et al. |
| 6,238,412 B1 | 5/2001 | Dubrul et al. |
| 6,245,078 B1 | 6/2001 | Ouchi |
| 6,258,115 B1 | 7/2001 | Dubrul |
| 6,544,278 B1 | 4/2003 | Vrba et al. |
| 6,569,181 B1 | 5/2003 | Burns |
| 6,620,179 B2 | 9/2003 | Brook et al. |
| 6,635,068 B1 | 10/2003 | Dubrul et al. |
| 6,635,070 B2 | 10/2003 | Leeflang et al. |
| 6,830,561 B2 | 12/2004 | Jansen et al. |
| 6,846,029 B1 | 1/2005 | Ragner et al. |
| 6,942,682 B2 | 9/2005 | Vrba et al. |
| 7,621,870 B2 | 11/2009 | Berrada et al. |
| 7,780,696 B2 | 8/2010 | Daniel et al. |
| 8,057,496 B2 | 11/2011 | Fischer, Jr. |
| 8,070,769 B2 | 12/2011 | Broome |
| 8,092,486 B2 | 1/2012 | Berrada et al. |
| 8,657,867 B2 | 2/2014 | Dorn et al. |
| 8,721,714 B2 | 5/2014 | Kelley |
| 8,784,442 B2 | 7/2014 | Jones et al. |
| 8,795,305 B2 | 8/2014 | Martin et al. |
| 8,956,384 B2 | 2/2015 | Berrada et al. |
| 9,028,401 B1 | 5/2015 | Bacich et al. |
| 9,125,683 B2 | 9/2015 | Farhangnia et al. |
| 9,126,016 B2 | 9/2015 | Fulton |
| 9,155,552 B2 | 10/2015 | Ulm, III |
| 9,173,668 B2 | 11/2015 | Ulm, III |
| 9,186,487 B2 | 11/2015 | Dubrul et al. |
| 9,358,037 B2 | 1/2016 | Farhangnia et al. |
| 9,259,237 B2 | 2/2016 | Quick et al. |
| 9,351,747 B2 | 5/2016 | Kugler et al. |
| 9,463,035 B1 | 10/2016 | Greenhalgh et al. |
| 9,717,514 B2 | 8/2017 | Martin et al. |
| 9,848,975 B2 | 12/2017 | Hauser |
| 9,849,014 B2 | 12/2017 | Kusleika |
| 9,962,178 B2 | 5/2018 | Greenhalgh et al. |
| 1,001,033 A1 | 7/2018 | Greenhalgh et al. |
| 1,001,626 A1 | 7/2018 | Hauser |
| 1,002,875 A1 | 7/2018 | Wallace et al. |
| 1,013,038 A1 | 11/2018 | Farhangnia et al. |
| 1,027,186 A1 | 4/2019 | Greenhalgh et al. |
| 2002/0032455 A1 | 3/2002 | Boock et al. |
| 2002/0173819 A1 | 11/2002 | Leeflang et al. |
| 2003/0083693 A1 | 5/2003 | Daniel et al. |
| 2003/0135258 A1 | 7/2003 | Andreas et al. |
| 2003/0153873 A1 | 8/2003 | Luther et al. |
| 2003/0176884 A1 | 9/2003 | Berrada et al. |
| 2003/0208224 A1 | 11/2003 | Broome |
| 2004/0098033 A1 | 5/2004 | Leeflang et al. |
| 2005/0085826 A1 | 4/2005 | Nair et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0283166 A1 | 12/2005 | Greenhalgh |
| 2005/0283186 A1 | 12/2005 | Berrada et al. |
| 2006/0042786 A1 | 3/2006 | West |
| 2006/0089533 A1 | 4/2006 | Ziegler et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0293696 A1 | 12/2006 | Fahey et al. |
| 2007/0112374 A1 | 5/2007 | Paul, Jr. et al. |
| 2007/0149996 A1 | 6/2007 | Coughlin |
| 2007/0213765 A1 | 9/2007 | Adams et al. |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desai et al. |
| 2010/0190156 A1 | 7/2010 | Van Wordragen et al. |
| 2010/0249815 A1 | 9/2010 | Jantzen et al. |
| 2011/0034987 A1 | 2/2011 | Kennedy |
| 2011/0118817 A1 | 5/2011 | Gunderson et al. |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1 | 11/2011 | Martin |
| 2012/0083824 A1 | 4/2012 | Berrada et al. |
| 2012/0083868 A1 | 4/2012 | Shrivastava |
| 2012/0271105 A1 | 10/2012 | Nakamura et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0226196 A1 | 8/2013 | Smith |
| 2013/0317589 A1 | 11/2013 | Martin et al. |
| 2013/0345739 A1 | 12/2013 | Brady et al. |
| 2014/0005712 A1 | 1/2014 | Martin et al. |
| 2014/0046133 A1 | 2/2014 | Nakamura et al. |
| 2014/0155980 A1 | 6/2014 | Turjman |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0164523 A1 | 6/2015 | Brady et al. |
| 2015/0164666 A1 | 6/2015 | Johnson et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2016/0022293 A1 | 1/2016 | Dubrul et al. |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2017/0086864 A1 | 3/2017 | Greenhalgh et al. |
| 2017/0112513 A1 | 4/2017 | Marchand et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |

(56) References Cited

U.S. PATENT DOCUMENTS

| | | | |
|---|---|---|---|
| 2017/0348014 | A1 | 12/2017 | Wallace et al. |
| 2018/0042624 | A1 | 2/2018 | Greenhalgh et al. |
| 2018/0042626 | A1 | 2/2018 | Greenhalgh et al. |
| 2018/0070968 | A1 | 3/2018 | Wallace et al. |
| 2019/0117244 | A1 | 4/2019 | Wallace et al. |
| 2019/0133622 | A1 | 5/2019 | Wallace et al. |
| 2019/0133623 | A1 | 5/2019 | Wallace et al. |
| 2019/0133624 | A1 | 5/2019 | Wallace et al. |
| 2019/0133625 | A1 | 5/2019 | Wallace et al. |
| 2019/0133626 | A1 | 5/2019 | Wallace et al. |
| 2019/0133627 | A1 | 5/2019 | Wallace et al. |

FOREIGN PATENT DOCUMENTS

| | | |
|---|---|---|
| GB | 2498349 | 7/2013 |
| WO | WO 00/32118 | 6/2000 |
| WO | WO 2009086482 | 7/2009 |
| WO | WO 2012/009675 | 1/2012 |
| WO | WO 2012/049652 | 4/2012 |
| WO | WO 2012162437 | 11/2012 |
| WO | WO 2017/058280 | 4/2017 |
| WO | WO2017189535 | 11/2017 |
| WO | WO2017189550 | 11/2017 |
| WO | WO2017189591 | 11/2017 |
| WO | WO 2017189615 | 11/2017 |
| WO | WO2017210487 | 12/2017 |
| WO | WO 2018049317 | 3/2018 |
| WO | WO 2019010318 | 1/2019 |
| WO | WO 2019094456 | 5/2019 |

OTHER PUBLICATIONS

Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Non-final office action dated Feb. 1, 2018 for U.S. Appl. No. 15/496,668.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Non-Final Office Action for U.S. Appl. No. 15/496,570, dated Aug. 9, 2017.
PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
Response to Non-Final Office Action for U.S. Appl. No. 14/496,786, filed Feb. 1, 2018.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Invitation to Pay Additional Fees for International Patent Appln. No. PCT/US2018/059607 dated Jan. 31, 2019.
Japanese Office action dated Mar. 19, 2019 for Japanese Application No. 2018535810 (with English Language translation).
International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Restriction Requirement filed Jul. 25, 2019 for U.S. Appl. No. 15/700,685.
Non-Final Office Action dated Aug. 23, 2019 for U.S. Appl. No. 15/700,685.
Non-Final Office Action dated Sep. 3, 2019 for U.S. Appl. No. 15/794,939.
Rule 71(3) Allowance for EP Patent Appln. No. 18174891.4 dated Jul. 30, 2019.
Office action dated Jun. 5, 2019 for Chinese application No. 2019053101871820, including partial English language translation provided by the foreign associate, received on Jul. 26, 2019.

(56) References Cited

OTHER PUBLICATIONS

Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Oct. 24, 2019 for U.S. Appl. No. 15/611,546.
Office action response filed Sep. 26, 2019 for Chinese Patent Application No. 2016800567527, no translation received.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.

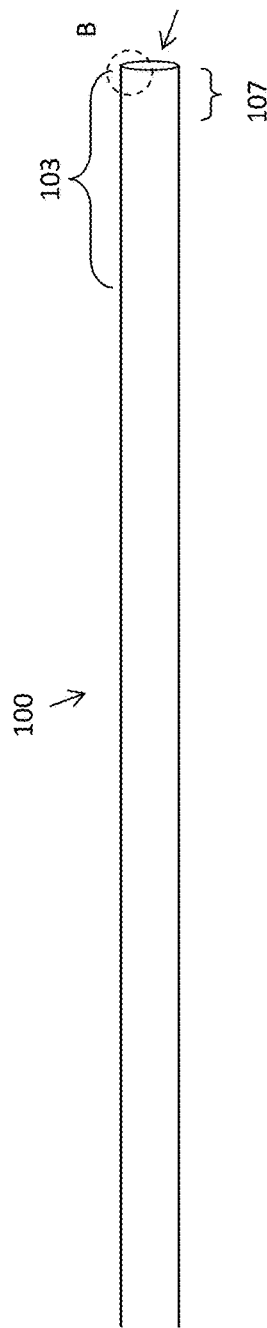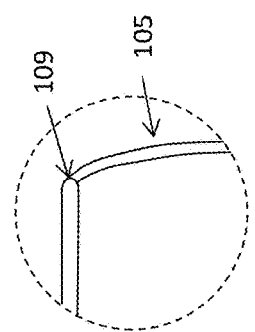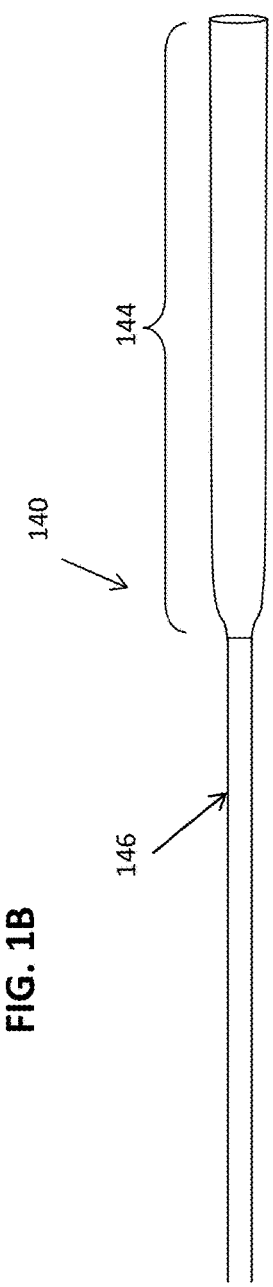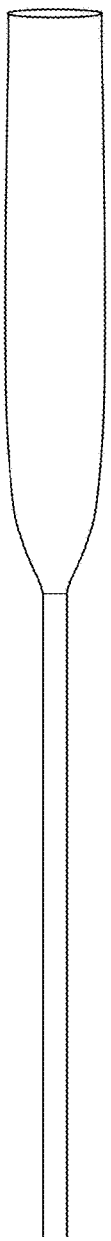
FIG. 1A
FIG. 1B
FIG. 1C
FIG. 1D

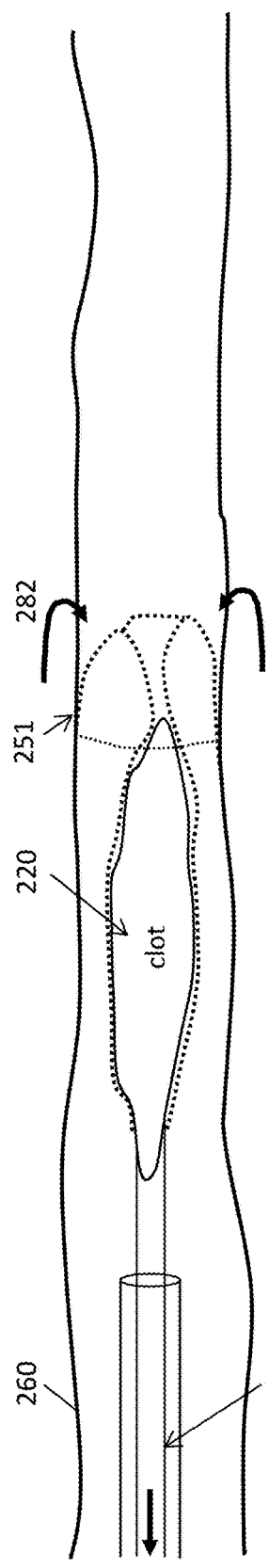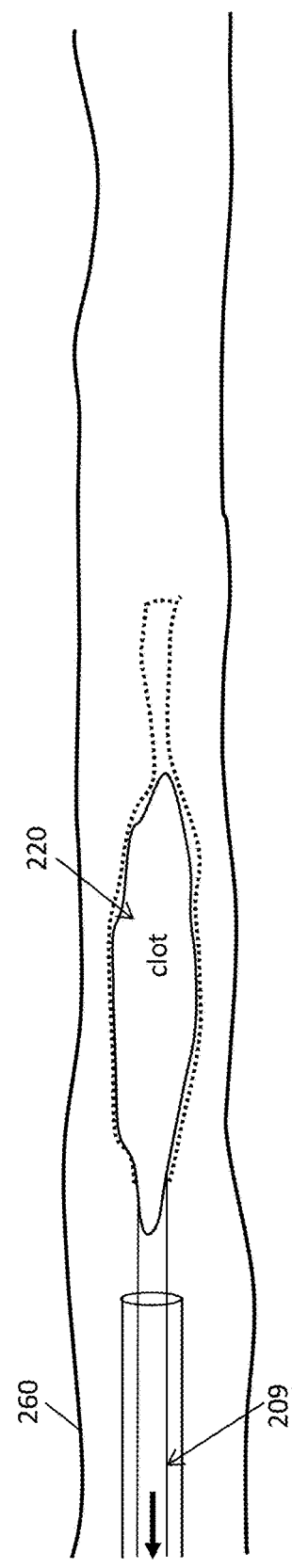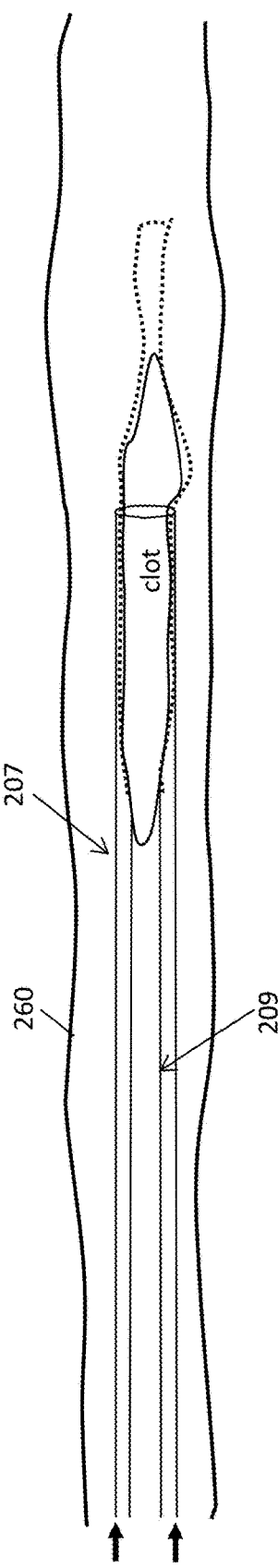

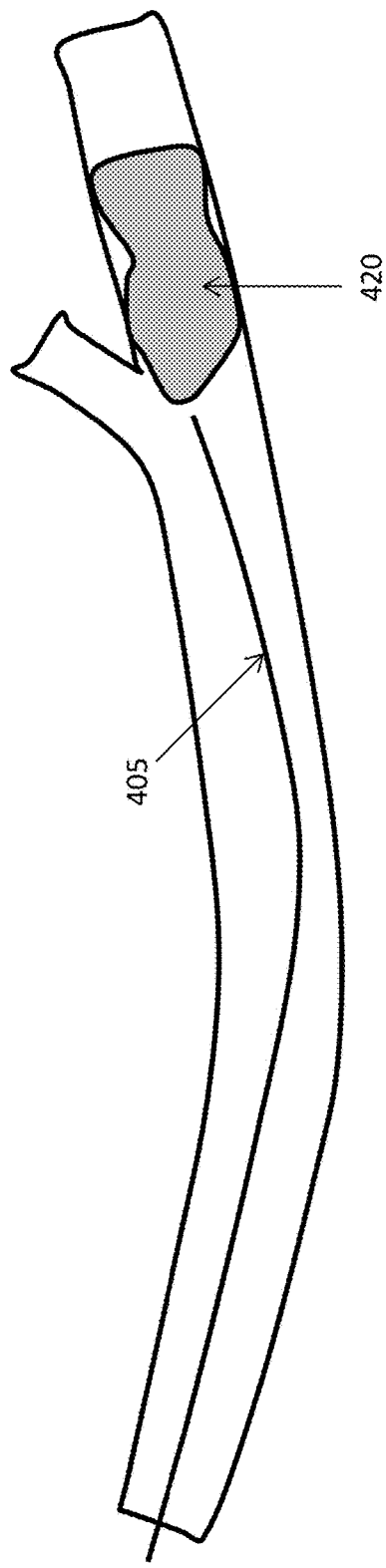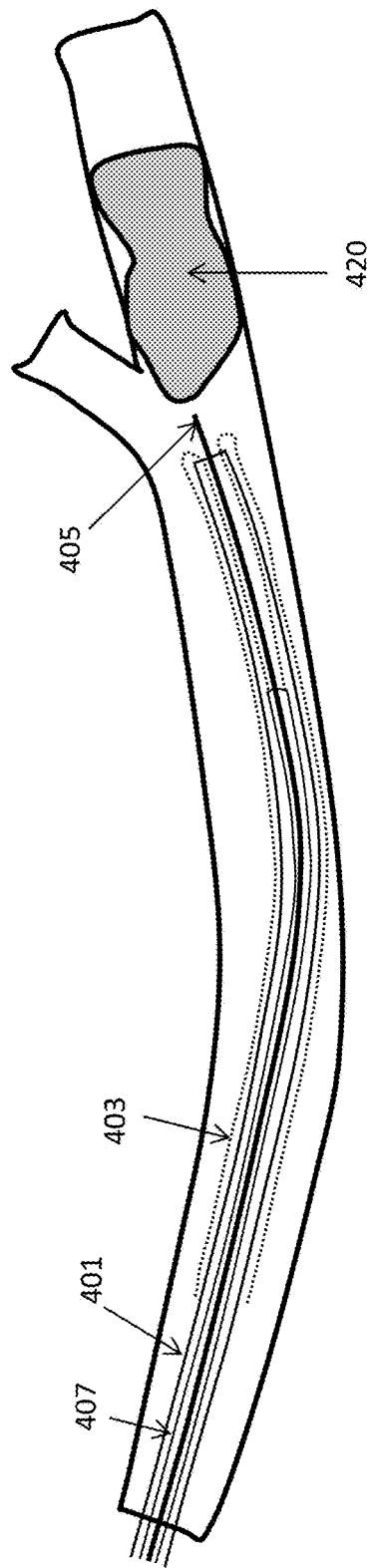
FIG. 4A
FIG. 4B

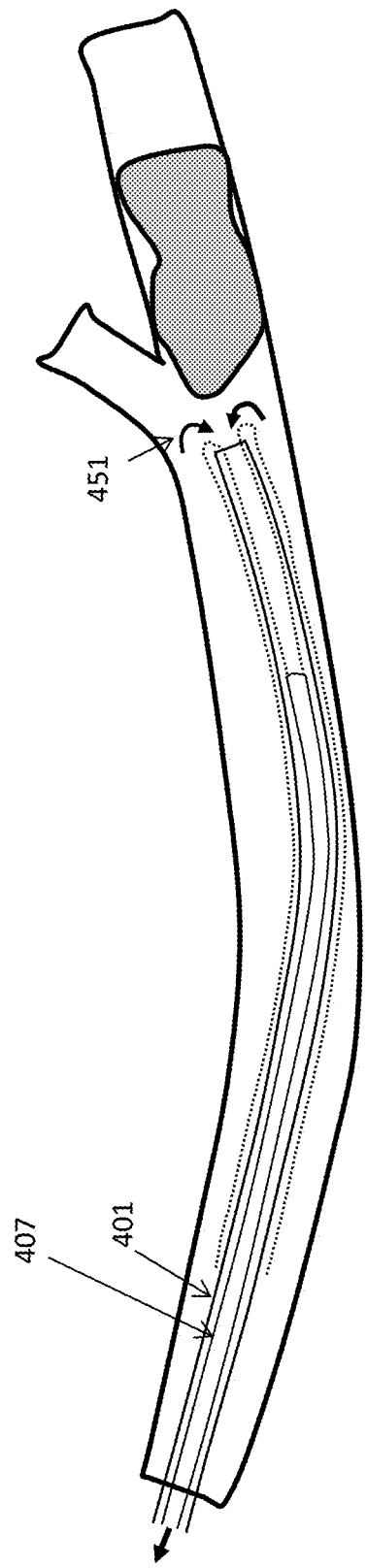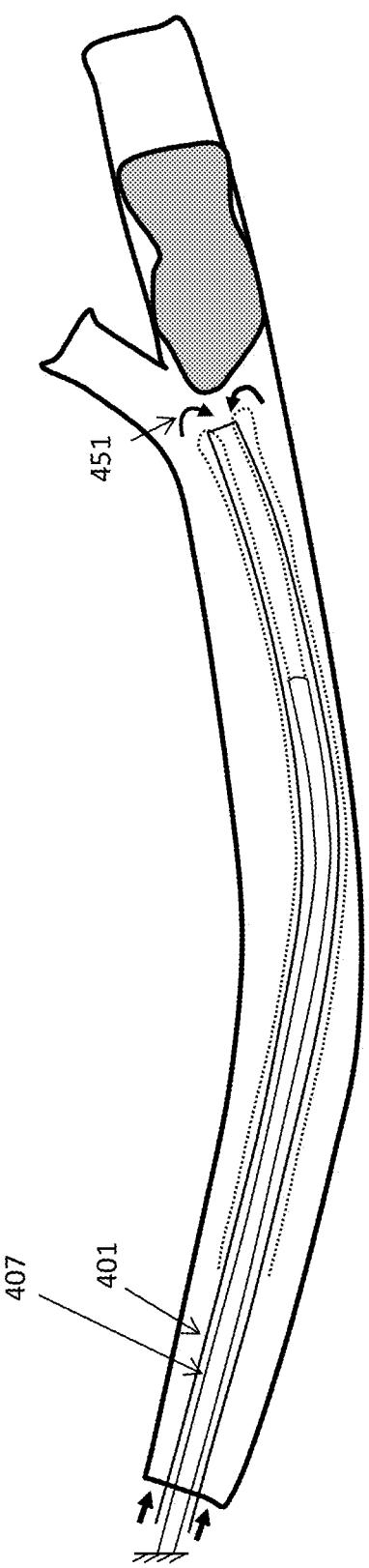

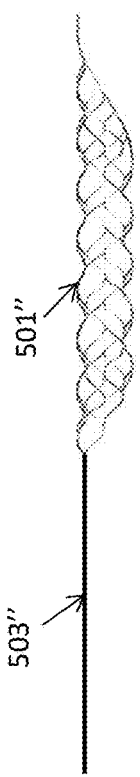
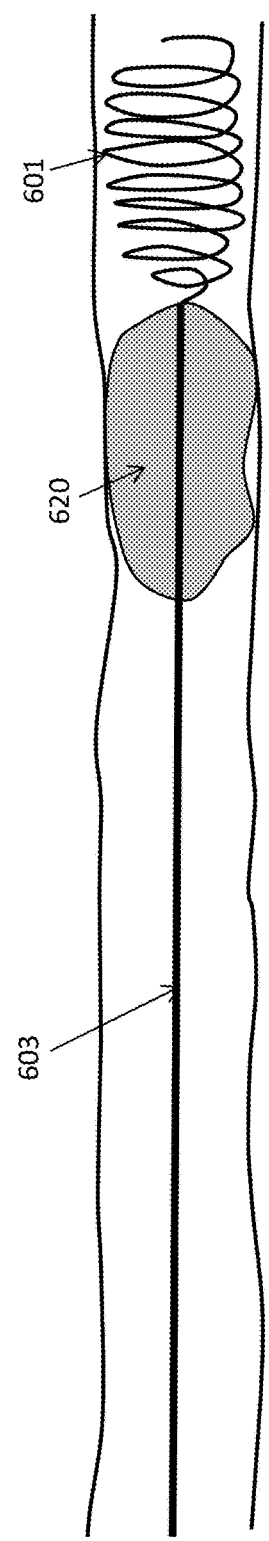
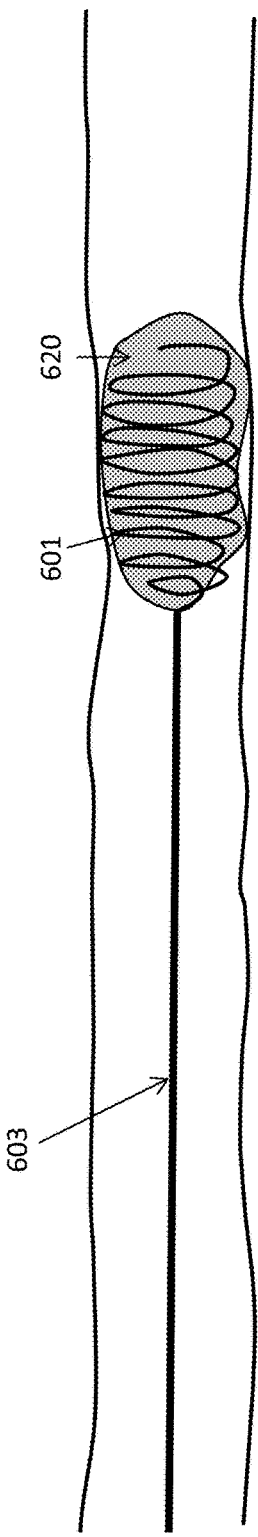
FIG. 5A
FIG. 5B
FIG. 5C
FIG. 6A
FIG. 6B

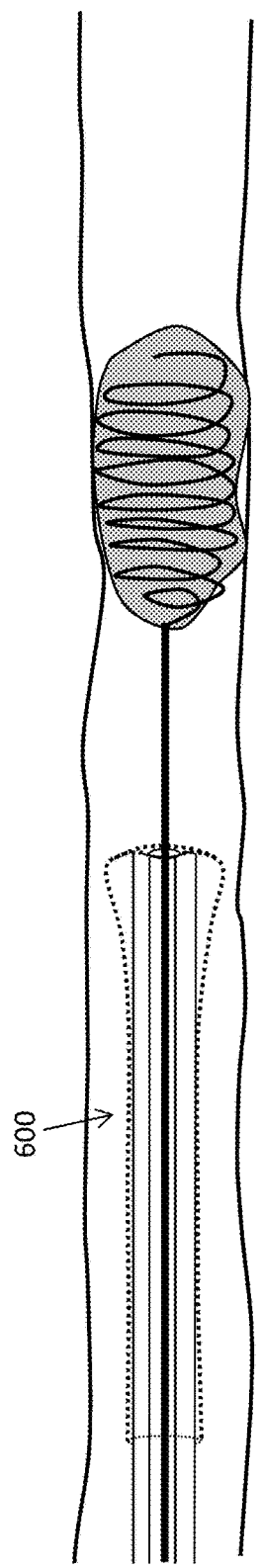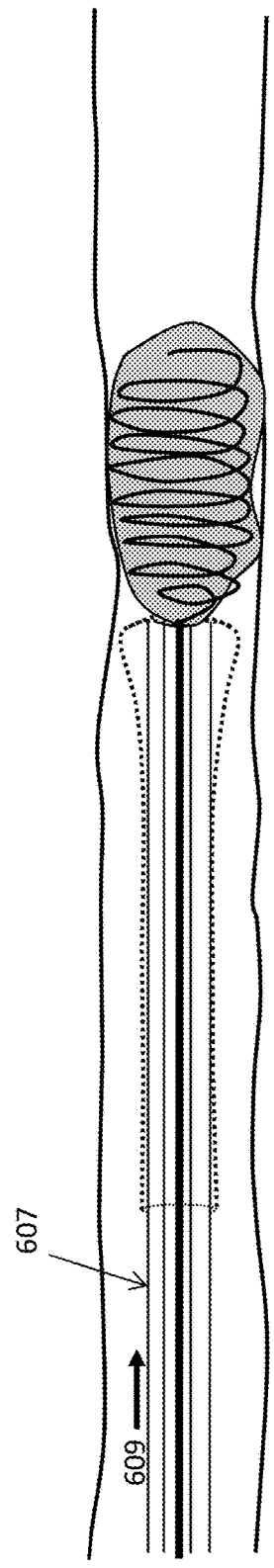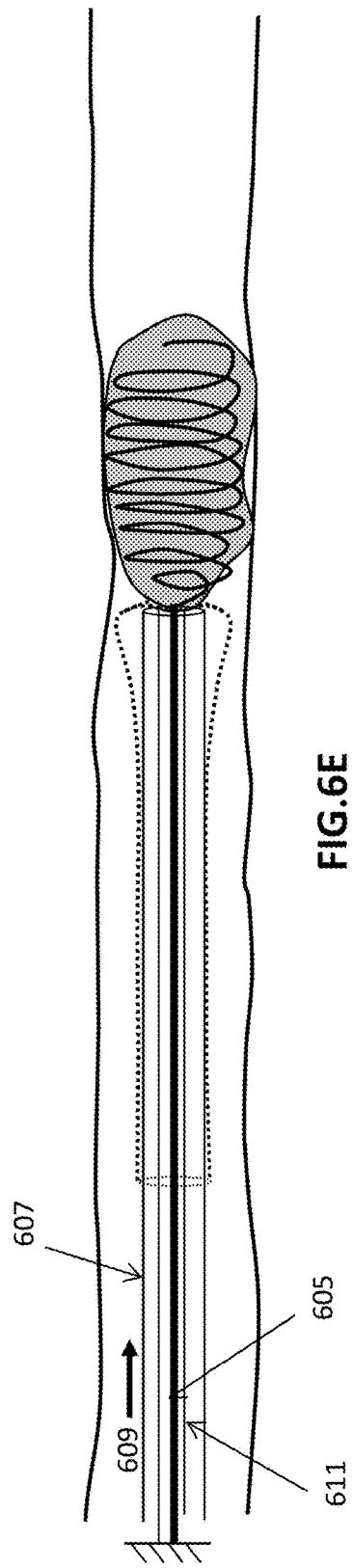

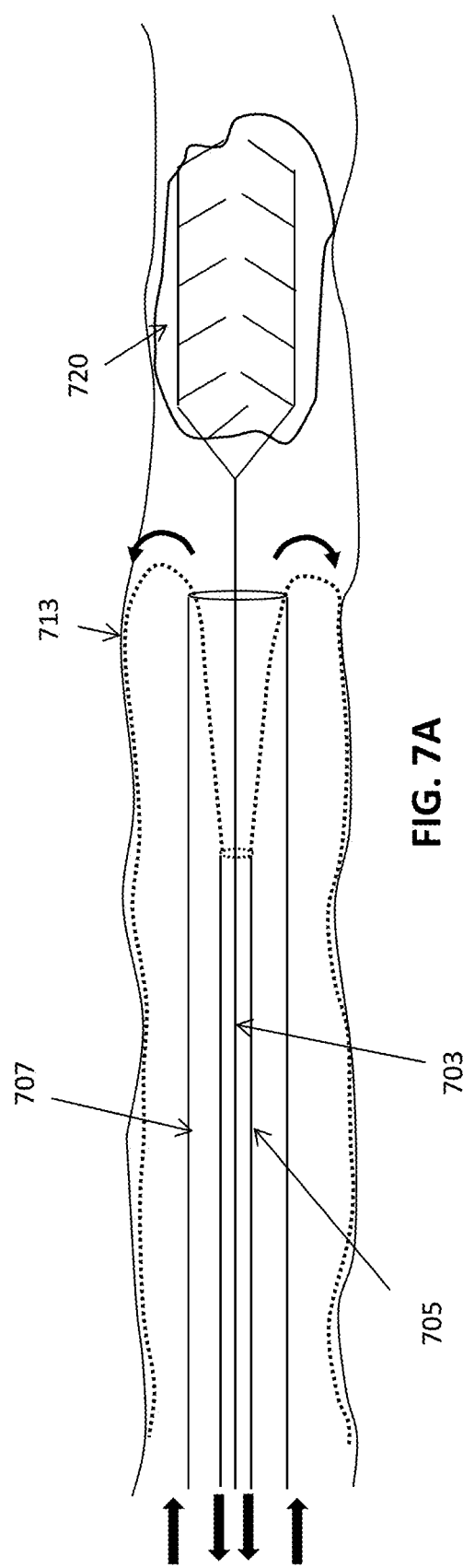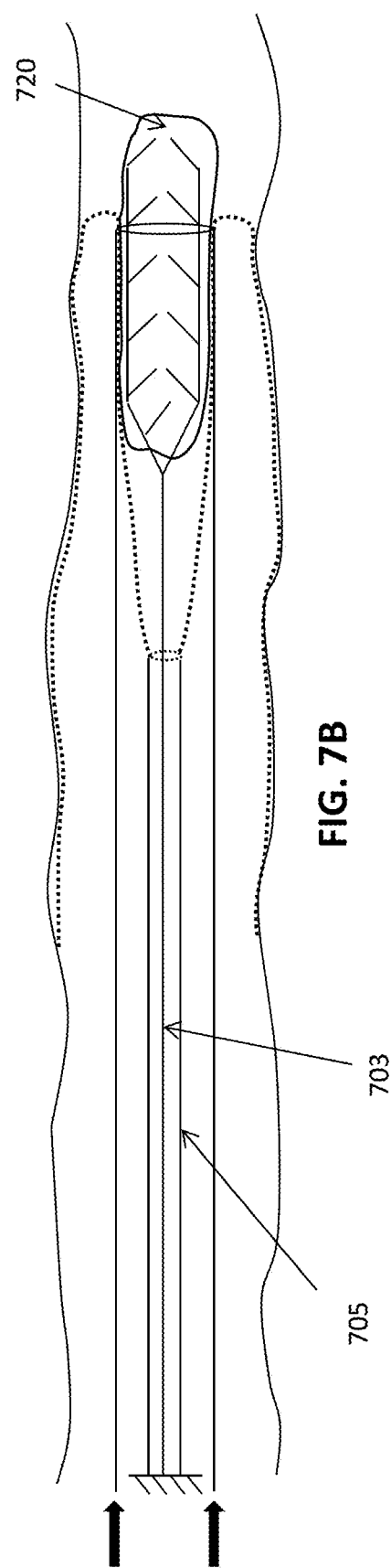

CLOT-ENGULFING MECHANICAL THROMBECTOMY APPARATUSES

CROSS REFERENCE TO RELATED APPLICATIONS

This patent application claims priority to U.S. provisional patent application No. 62/327,024, filed on Apr. 25, 2016 and titled "DOZER THROMBECTOMY SYSTEM"; U.S. provisional patent application No. 62/345,152, filed on Jun. 3, 2016, and titled "DOZER THROMBECTOMY SYSTEM 2"; and U.S. provisional patent application No. 62/357,677, filed on Jul. 1, 2016, and titled "DOZER THROMBECTOMY SYSTEM 3".

This patent application may be related to U.S. patent application Ser. No. 15/291,015, filed on Oct. 11, 2016, titled "MECHANICAL THROMBECTOMY APPARATUSES AND METHODS", which is a continuation of U.S. patent application Ser. No. 15/043,996, filed Feb. 15, 2016, now U.S. Pat. No. 9,463,035, which claims priority to each of the following provisional patent applications: U.S. Provisional Patent Application No. 62/284,300, filed Sep. 28, 2015; U.S. Provisional Patent Application No. 62/284,752, filed Oct. 8, 2015; and U.S. Provisional Patent Application No. 62/245,560, filed Oct. 23, 2015.

Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses described herein relate to mechanical removal of objects from within a body. In particular, described herein are mechanical thrombectomy apparatuses and methods for removing a clot, including removing a clot captured by a clot capture device (e.g., a clot engaging member on the distal end of an elongate manipulator) with a rolling tractor that pulls the clot and clot capture device into a catheter.

BACKGROUND

It is often desirable to remove tissue from the body in a minimally invasive manner as possible, so as not to damage other tissues. For example, removal of tissue from within a vasculature, such as blood clots, may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Mechanical thrombectomy devices may be particularly advantageous. Depending on the size, location and extent of a clot, it may also be particularly advantageous to mechanical retrieve and break apart the clot in a manner that is both safe and effective. There is a definite need for a thrombectomy device, and particularly a mechanical thrombectomy device that can be more effective in removing tissue such as clots from within a body. Described herein are apparatuses (devices, systems and kit) and methods of using them that may address the needs and problems discussed above.

SUMMARY OF THE DISCLOSURE

Described herein are mechanical thrombectomy apparatuses (devices, systems, etc.) and methods of using them to remove a thrombus, e.g., clot, including safely and easily removing a clot that is captured in a second clot-grabbing (e.g., thrombectomy) apparatus. The mechanical thrombectomy apparatuses described herein may be inverting tractor thrombectomy apparatuses. An inverting tractor apparatus may include a tractor (tractor region, tractor portion, etc.) comprising a flexible tube of material that inverts as it rolls over itself at a distal end. The tractor may be inverted and/or rolled over the end of a catheter. Thus, the flexible tractor may invert and fold back into itself and may be drawn into a catheter portion in a conveyor-like motion as it rolls around to transition from an outward-facing region of the tractor on an outside of the catheter to an inward-facing region within the lumen of the catheter. The rolling motion may draw a clot and/or clot connected to a clot-grabbing apparatus within a vessel into the catheter, which may also compress and/or macerate the clot. The apparatus, including the clot, and in some variations clot and a clot engaging member engaged with the clot, may then be removed from the body.

Any of these apparatuses may include, or may be used as part of a system with, a clot capture device having a clot engaging member (e.g., a "stentriever") at the distal end of an elongate manipulator.

The mechanical thrombectomy apparatuses described herein may include pre-loaded inverting tractor thrombectomy apparatuses (e.g., devices, systems, etc.). Described herein are mechanical thrombectomy apparatuses, including inverting tractor thrombectomy apparatuses that may engulf a clot prior to pulling it (e.g., into the apparatus) and may be used in combination with other systems. Such apparatuses may invert over clot first, and may then pull the clot into the catheter. Any of these apparatuses may also incorporate aspiration.

Described herein are mechanical thrombectomy systems that include an elongate inversion support (typically comprising a catheter), a flexible tractor that inverts over the distal end opening of the elongate inversion support, a puller extending proximally to roll and invert the tractor into the distal end opening, and a clot engaging member on the distal end of an elongate manipulator. The puller and tractor are configured to pass the elongate manipulator through a lumen extending continuously through the puller and the tractor. As described above, in operation, this may be used to slide the rolling thrombectomy portion (e.g., the elongate inversion support, a flexible tractor and a puller) over the elongate manipulator of the clot capture device (e.g., clot engaging member on the distal end of an elongate manipulator).

For example, described herein are mechanical thrombectomy systems including: an elongate inversion support comprising a catheter having a distal end and a distal end opening; a tractor comprising a flexible tube that extends distally in an un-inverted configuration within the catheter, inverts over the distal end opening of the catheter and extends proximally in an inverted configuration along the distal end of the catheter, wherein the tractor is configured to invert by rolling over the distal end opening of the catheter when a first end of the tractor is pulled proximally within the catheter; a puller connected to the first end of the tractor extending proximally; a clot engaging member on the distal end of an elongate manipulator; and a lumen extending continuously through the puller and the tractor and configured to pass the expandable elongate manipulator.

In any of these apparatuses (e.g., systems, devices, etc.), the tractor may be sufficiently soft such that without support from the catheter, it collapses radially under an axial compression of less than a small force (e.g., less than 50 g of force, 100 g of force, less than 150 g of force, less than 200 g of force, less than 250 g of force, less than 300 g of force, etc.) when inverting.

Further, in any of these apparatuses, the tractor may be biased to expand to greater than the outer diameter of the catheter in the inverted configuration and is biased to expand to greater than the inner diameter of the catheter in the un-inverted configuration.

The clot engaging member may be expandable. For example, the clot engaging member may be one or more of: a coil, a snare, a basket, or a frame. The elongate manipulator may be a wire, tube (e.g., hypotube), rod, etc.

Any appropriate flexible tractor may be used. For example, the tractor may be one or more of: a braided material, a knitted material, or a woven material. The tractor is typically a tube of material. The tractor may comprise steel, polyester, nylon, expanded Polytetrafluoroethylene (ePTFE), Nitinol, or a fabric.

The catheter of the elongate inversion support may extend the full length of the inversion support, or it may be just at the end of the elongate inversion support. The catheter may be soft (e.g., appropriate for neurovascular use), however the tip may be harder, to resist collapse. For example, the material hardness of catheter decreases over the distal end of the catheter until the distal end opening, wherein the distal end opening has a material hardness that is greater than a material hardness of a region immediately proximal to the distal end, further wherein the distal end opening has a rounded lip profile.

The tractor may be lubricious and/or may comprise one or more coatings from the group of: a lubricious coating, a metal coating, a heparin coating, an adhesive coating, and a drug coating. The tractor may be any appropriate length (e.g., between about is 3 cm to 100 cm long, between about 10 cm to 200 cm long, between about 3 cm to 50 cm long, between about 200 cm to 500 cm long, etc.).

Any of these apparatuses may be configured to controllably deploy the tractor, which may be held compressed and/or against the catheter of the elongate inversion support until being deployed. For example, any of these apparatus may include a releasable attachment between the tractor and an outer surface of the catheter (e.g., a tractor hold), wherein the releasable attachment is configured to release when the tractor is pulled (e.g., proximally by the puller) with a force that is greater than a predetermined force threshold. The deployment force threshold may be between 50 g and 500 g of force (e.g., between 50 g and 400 g of force, between 100 g and 400 g of force, etc.).

Any of these apparatuses may include a sleeve extending over the catheter and tractor. The sleeve may be an outer or intermediate catheter.

A mechanical thrombectomy system for removing a clot from within a vessel may include: an elongate inversion support comprising a catheter having a distal end and a distal end opening; a tractor comprising a flexible tube that extends distally in an un-inverted configuration within the catheter, inverts over the distal end opening of the catheter and extends proximally in an inverted configuration along the distal end of the catheter, wherein the tractor is configured to invert by rolling over the distal end opening of the catheter when a first end of the tractor is pulled proximally within the catheter; a puller extending proximally within the catheter and connected to the first end of the tractor; an expandable clot engaging member on the distal end of an elongate manipulator, wherein the expandable clot engaging member comprises one or more of: a coil, a snare, a basket, or a frame; and a lumen extending continuously through the puller and the tractor and configured to pass the expandable elongate manipulator.

In operation, these systems may be used to withdraw a thrombus (clot) from within a vessel, including peripheral vessels or neurovascular vessels. For example, described herein are methods of removing a clot from within a vessel using a mechanical thrombectomy apparatus. These methods generally include rolling the tractor into the catheter by pulling proximally on the tractor (e.g., by pulling on a puller that extends proximally and is attached to the first end of the tractor within the catheter) to roll the tractor into the catheter. The conveyer-belt like tractor motion, either alone or in conjunction with aspiration applied from the proximal end through the mechanical thrombectomy apparatus (e.g., catheter) and/or an outer catheter within which the mechanical thrombectomy apparatus is passed, may be used to pull a clot into the catheter. Typically when drawing the clot into the apparatus (e.g., into the catheter portion of the apparatus), the clot, or a clot and additional clot engaging member coupled to the clot, may be compressed as it is drawn into the apparatus.

In some cases, the clot may clog or jam in the apparatus. Described herein are methods of removing a clot from within a vessel using a mechanical thrombectomy apparatus, including methods configured to avoid or correct jamming and/or clogging of the apparatus. The method may include: positioning a distal end of the mechanical thrombectomy apparatus adjacent to the clot within a vessel, wherein the mechanical thrombectomy apparatus includes a tractor region that extends along a distal region of a catheter and inverts over a distal end of the catheter so that a first end of the tractor extends proximally within the catheter; pulling the first end of the tractor proximally within the catheter to roll the tractor over the distal end of the catheter so that the tractor inverts over the distal end of the catheter and pull the clot into the catheter with the inverting tractor; withdrawing the catheter proximally away from the tractor and clot when the tractor jams on the distal end of the catheter; pulling the first end of the tractor proximally so that the tractor inverts over the clot within the vessel without rolling over the distal end opening of the catheter; and withdrawing the tractor and clot proximally from the vessel.

Any of the methods described herein may include releasing the tractor from a locked or secured position on the outside of the catheter of the apparatus. Thus, any of these apparatuses used herein may include a tractor hold that releasably secures the tractor to the outside of the catheter. For example, any of the methods described herein may include disengaging a second end of the tractor from a tractor hold that secures the second end of the tractor to an outer surface of the catheter by pulling the tractor proximally with a force greater than a deployment force and expanding the tractor against the vessel wall, wherein the second end of the tractor is disengaged before pulling the first end of the tractor proximally.

Once the clot and/or clot engaging member has been engulfed by the tractor, it may then be withdrawn back into the catheter, without requiring the tractor to invert over the catheter. For example, any of the methods described herein may also or alternatively include pulling proximally on the tractor to draw the tractor and clot into the catheter.

Pulling the first end of the tractor proximally within the catheter to roll the tractor over the distal end of the catheter may comprise advancing the catheter while pulling the first end of the tractor. Alternatively or additionally, pulling the first end of the tractor proximally so that the tractor inverts over the clot may further comprise pulling the catheter proximally with the first end of the tractor. Alternatively or additionally, pulling the first end of the tractor proximally so that the tractor inverts over the clot may comprise pulling a puller at the proximal end of the mechanical thrombectomy apparatus proximally.

Withdrawing the catheter proximally away from the tractor may comprise pulling the catheter proximally a short distance or a substantial distance. For example, the catheter may be pulled proximally only sufficiently far to disengage the jam of the clot (and/or clot engaging member) from the catheter distal end opening. Alternatively or additionally, withdrawing the catheter proximally away from the tractor (the tractor distal-facing end) may include pulling the catheter beyond a second end of the tractor that is outside of the catheter.

Alternatively or additionally, the catheter may be pulled proximally with the first end of the tractor (e.g., the tractor puller) as the tractor is pulled proximally so that the tractor inverts over the clot within the vessel without rolling over the distal end opening of the catheter.

In any of the methods described herein the tractor may be expanded to that all or a portion of the tractor contacts the wall of the vessel. Thus, the tractor may be expanded when released (e.g., from the tractor hold) to contact the wall of the vessel. Any of the tractors described herein may be biased (e.g., heat set, etc.) so that it expands (when over the catheter) to approximately 1× or more (e.g., 1.1×, 1.2×, 1.3×, 1.4×, 1.5×, etc.) the diameter of the vessel. Contact between the vessel wall and the tractor may provide resistance that enhances the ability of the tractor to invert when the first end of the tractor is pulled proximally without inverting over the distal end opening of the catheter. Pulling the first end of the tractor proximally so that the tractor inverts over the clot may comprise pulling the first end of the tractor when the tractor has expanded to contact the vessel wall.

In any of the methods described herein, a guidewire, catheter or the like may be used to position the apparatus near, adjacent to, or on the clot. For example, positioning the distal end of the mechanical thrombectomy apparatus adjacent to the clot may comprise sliding the mechanical thrombectomy apparatus over a guidewire or catheter passing through a lumen in the mechanical thrombectomy apparatus.

A method of removing a clot from within a vessel using a mechanical thrombectomy apparatus may include: positioning a distal end of the mechanical thrombectomy apparatus adjacent to the clot within a vessel, wherein the mechanical thrombectomy apparatus includes a tractor region that extends along a distal region of a catheter and inverts over a distal end of the catheter so that a first end of the tractor extends proximally within the catheter; disengaging a second end of the tractor from a tractor hold that secures the second end of the tractor to an outer surface of the catheter by pulling the tractor proximally with a force greater than a deployment force and expanding the tractor against the vessel wall; pulling the first end of the tractor proximally within the catheter to roll the tractor over the distal end of the catheter so that the tractor inverts over the distal end of the catheter and pull the clot into the catheter with the inverting tractor; withdrawing the catheter proximally away from the tractor and clot when the tractor jams on the distal end of the catheter; pulling the tractor and clot proximally so that the tractor inverts over the clot within the vessel without rolling over the distal end opening of the catheter; pulling proximally on the tractor to draw the tractor and clot into the catheter; and withdrawing the tractor and clot proximally from the vessel.

Also described herein are methods of removing a clot from within a vessel using a mechanical thrombectomy apparatus in which a secondary clot-grabbing device (e.g., generally referred to herein as a clot engaging member), which may be a secondary device or a part of the mechanical thrombectomy apparatuses described herein, is removed with the clot. Any appropriate clot engaging member may be used. In particular, a clot engaging member may include an expandable/compressible clot engaging member that is configured a frame or wire. For example, a clot engagement member may be an expandable coil or plurality of coils, snare, basket, or frame. Any of these clot engagement members may include an elongate manipulator (e.g., an elongate wire, catheter, shaft, member, etc.) attached to the clot engagement member, such as the proximal end of the clot engagement member.

Any of the methods described herein may include tracking over the clot engaging member, including sliding over the elongate member attached to the clot engagement member. The mechanical thrombectomy apparatus may be guided to the clot and/or clot engagement member by sliding distally over an elongate member attached to a clot engagement member that has been previously coupled with a clot.

The clot engagement member may be coupled to the clot by passing into and/or through the clot. For example, the clot engagement member may be passed into the clot where it may engage with the clot material and expanded into the clot. Alternatively or additionally, the clot engagement member may be passed through the clot and expanded distally of the clot so that it may drive the clot proximally when the clot engagement member is pulled proximally, e.g., by pulling proximally on the elongate member coupled to the clot engagement member.

For example a method of removing a clot from within a vessel using a mechanical thrombectomy apparatus may include: engaging the clot with a clot engaging member on the distal end of an elongate manipulator; sliding the mechanical thrombectomy apparatus over the elongate manipulator to position the distal end of the mechanical thrombectomy apparatus adjacent to the clot, wherein the mechanical thrombectomy apparatus includes a tractor region that extends along a distal region of a catheter and inverts over a distal end of the catheter so that a first end of the tractor extends proximally within the catheter; pushing the catheter distally while holding the first end of the tractor within the catheter fixed relatively to the elongate manipulator so that the tractor rolls and inverts over the distal end of the catheter and pulls the clot and the clot engaging member into the catheter with the inverting tractor; and withdrawing the mechanical thrombectomy apparatus, clot and clot engaging member proximally from the vessel.

As mentioned, the clot engaging member may engage with the clot by expanding into the clot and/or beyond the clot. For example, engaging the clot with the clot engaging member on the distal end of the elongate manipulator may comprise expanding the engaging member within the clot. Engaging the clot with the clot engaging member on the distal end of the elongate manipulator may comprise expanding the engaging member on a distal side of the clot. In general, engaging the clot with the clot engaging member on the distal end of the elongate manipulator may comprise expanding the engagement member. For example, the engaging member may comprise an expandable coil(s), snare, basket, or frame.

In any of these methods in which a clot engaging member is used with the rolling mechanical thrombectomy apparatus, the apparatus may be advanced distally over the apparatus to capture the clot and clot engaging member. For example, in any of these methods pulling the first end of the tractor proximally may comprise advancing the catheter distally as the tractor is pulled proximally. Engulfing the clot and/or clot engaging member by advancing distally over the clot and/or clot engaging member may be particularly beneficial compared to methods in which the clot and clot engaging member are drawn proximally to be engulfed.

In any of these apparatuses, pulling the first end of the tractor proximally may comprise pulling a puller proximally wherein the puller is coupled to the first end of the tractor. Alternatively or additionally, pulling the first end of the tractor proximally may comprise pulling the elongate manipulator proximally with the first end of the tractor.

Any of these methods may also include releasing the tractor from the catheter. For example, any of these methods may include disengaging a second end of the tractor from a tractor hold that secures the second end of the tractor to an outer surface of the catheter by pulling the tractor proximally with a force greater than a deployment force and expanding the tractor against the vessel wall.

A method of removing a clot from within a vessel using a mechanical thrombectomy apparatus may include: engaging the clot with a clot engaging member on the distal end of an elongate manipulator; sliding the mechanical thrombectomy apparatus over the elongate manipulator to position the distal end of the mechanical thrombectomy apparatus adjacent to the clot, wherein the mechanical thrombectomy apparatus includes a tractor region that extends along a distal region of a catheter and inverts over a distal end of the catheter so that a first end of the tractor extends proximally within the catheter; sliding the mechanical thrombectomy apparatus over the elongate manipulator to position the distal end of the mechanical thrombectomy apparatus adjacent to the clot, wherein the mechanical thrombectomy apparatus includes a tractor region that extends along a distal region of a catheter and inverts over a distal end of the catheter so that a first end of the tractor extends proximally within the catheter; and withdrawing the mechanical thrombectomy apparatus, clot and clot engaging member proximally from the vessel.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1H illustrate an example of an apparatus for mechanically removing an object such as a clot form a body region (e.g., a rolling mechanical thrombectomy apparatus). FIG. 1A shows an example of an elongate inversion support portion of an apparatus, configured as a catheter portion. For example, at least the distal end of the elongate inversion support may be configured as a catheter. FIG. 1B shows an enlarged view of a distal end (opening) of the catheter of the elongate inversion support of FIG. 1A, showing the aperture formed by the distal end opening; FIG. 1C shows an example of a distal tractor region of a flexible tube (tractor tube) extending from a puller (the puller in this example is configured as a catheter. The tractor is shown in a first (e.g., un-inverted) configuration) and may be biased open, e.g., by heat setting, to have an outer diameter that is greater than the inner diameter of the catheter of the elongate inversion support, as shown in FIG. 1D. FIG. 1D shows the same distal tractor region of FIG. 1C with the expandable first end region expanded. This first configuration may be compressed down into the elongate inversion support and the distal end inverted over the catheter portion of the elongate inversion support, as shown in FIG. 1E. In FIG. 1E, the assembled mechanical thrombectomy apparatus with the elongate inversion support and the flexible tube forming the tractor is shown. The tractor extends through the catheter of the elongate inversion support and doubles back over the distal end opening of the catheter and extends over the outer diameter of the catheter. The outer portion of the tractor (extending along the outer diameter of the catheter) may be held in a collapsed configuration (as shown in FIG. 1E), or it may be expanded, as shown in FIG. 1F. Thus, the tractor may be biased so that in the second configuration (inverted over the distal end of the catheter), the tractor has a 'relaxed' outer diameter that is greater than the outer diameter of the catheter of the elongate inversion support. FIGS. 1G and 1H illustrate the use of the apparatus of FIGS. 1E and 1F to remove a clot by drawing the flexible tube proximally and/or advancing the catheter distally towards the clot so that the expandable first end region inverts as it is drawn into the distal end of the catheter, pulling the clot into the catheter.

In an alternative variation of a tractor and puller, the tractor is attached to the distal end of a tapered or narrow puller; the distal end region is tapered, and includes a radiopaque marker at or near the attachment site to the tractor; the tractor may be knitted, braided, woven, etc. Thus, in some variations the distal end region of the puller may have a greater flexibility than the proximal end of the puller. The puller may be hollow (e.g., a catheter or hypotube) or solid (e.g., like a wire).

FIGS. 2A-2G illustrate a method of capturing a clot with a rolling mechanical thrombectomy apparatus after it has jammed or clogged the catheter of the rolling mechanical thrombectomy apparatus.

Figure 2A:
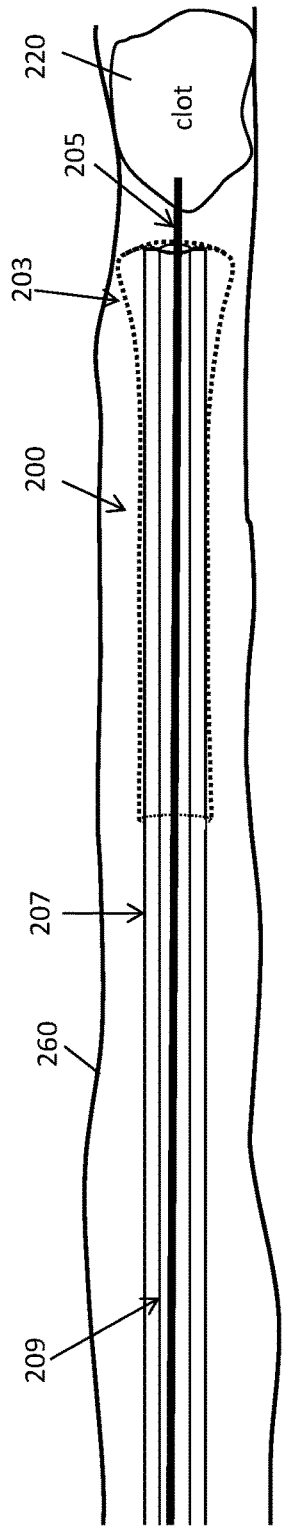
Figure 2B:
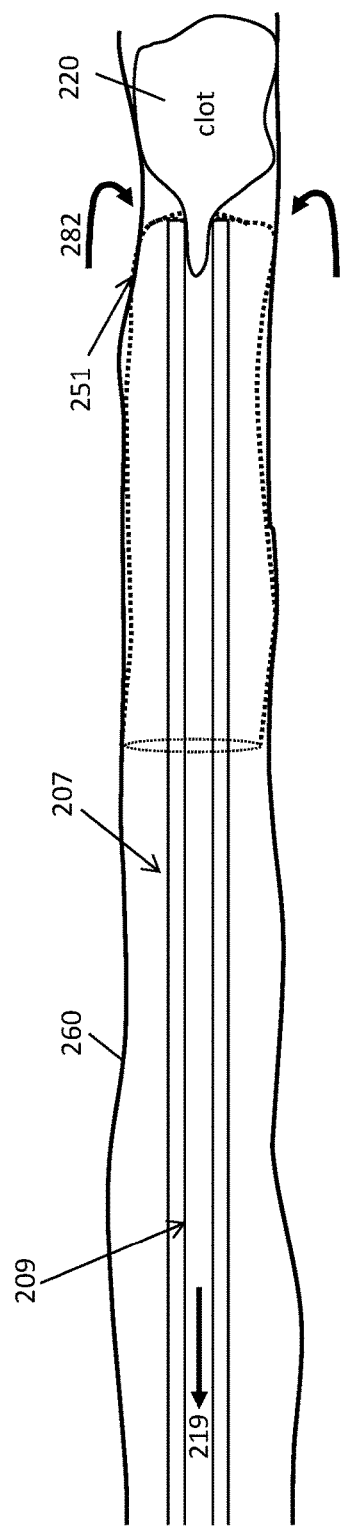
Figure 2C:
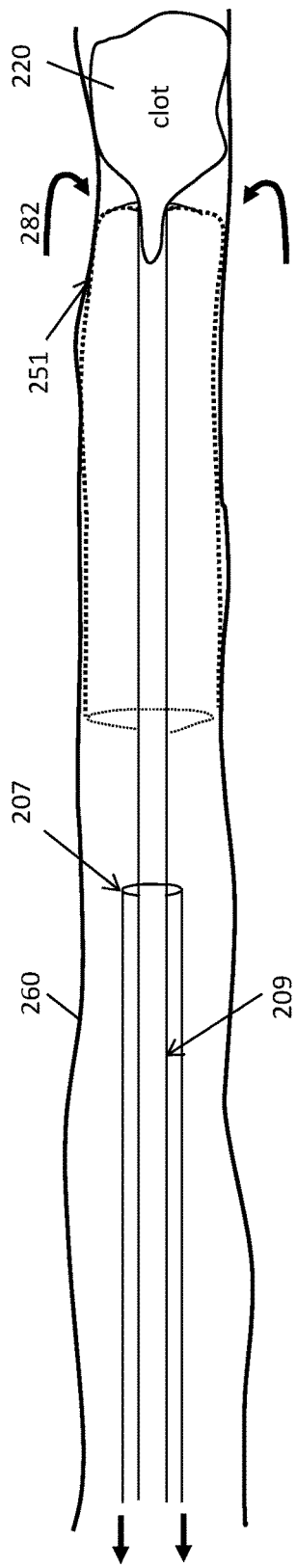
Figure 2G:
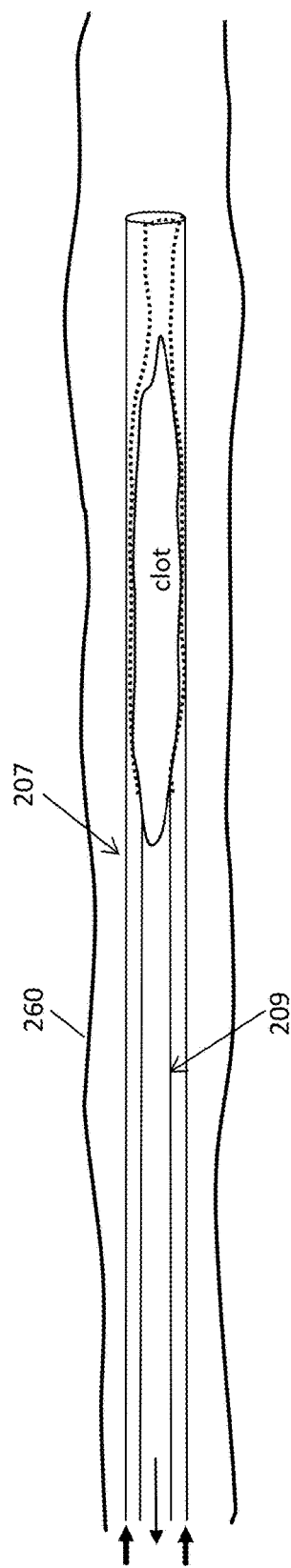
Figure 3A:
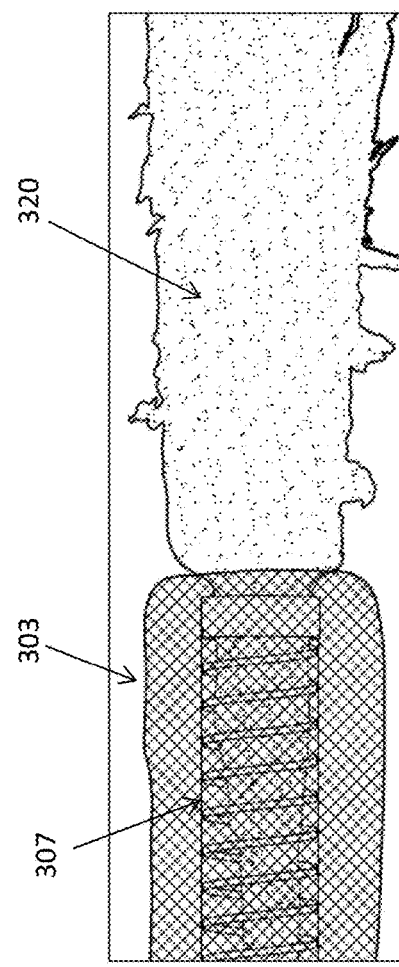
Figure 3B:
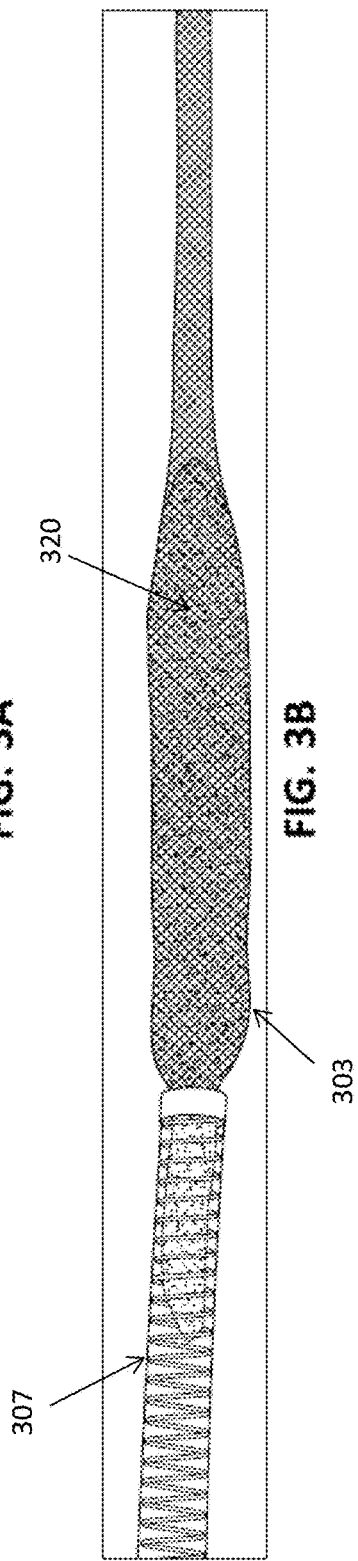

FIG. 3A illustrates an example of a rolling mechanical thrombectomy apparatus in which the clot has jammed while rolling the tractor into the distal end opening of the catheter portion of the rolling mechanical thrombectomy apparatus, similar to that shown in FIG. 2B. FIG. 3B illustrates an example of the clot engulfed by the tractor as illustrated in FIGS. 2C-2F. As shown in FIGS. 2F and 2G, the clot and tractor may then be drawn proximally out of the vessel, including by drawing proximally into the catheter first.

FIGS. 4A-4G illustrate an example of a rolling mechanical thrombectomy apparatus in which the clot has jammed while rolling the tractor into the distal end opening of the catheter portion of the rolling mechanical thrombectomy apparatus.

FIGS. 5A-5C illustrate examples of clot engaging members coupled to elongate manipulators that may be used with any of the apparatuses described herein.

FIGS. 6A-6H illustrate a method of capturing a clot engaged with a clot engagement member by advancing a rolling mechanical thrombectomy apparatus over the clot and clot engagement member.

FIG. 6I illustrates an example of a mechanical thrombectomy system for removing a clot from within a vessel.

FIGS. 7A-7B illustrate a method of capturing a clot engaged with a clot engagement member as described herein.

DETAILED DESCRIPTION

In general, described herein are mechanical thrombectomy apparatuses and methods of using them to remove clots. The mechanical thrombectomy apparatuses descried herein may have an inverting tractor region and an elongate inversion support having a distal annulus over which the tractor rolls and inverts over itself. Any of these apparatuses and methods of using them may be configured to prevent premature deployment of the tractor. The elongate inversion support may be a catheter having a distal end opening. The tractor may comprise a flexible tube that may be formed of a sheet having openings, or may be a woven, braided, knitted, etc. material such as a fiber. The tractor may extend longitudinally within the elongate inversion support and may and double back (e.g., invert) over the annulus of the elongate inversion support (e.g., the distal end of a catheter) so that it extends along the midline of the apparatus; when the elongate inversion support is a catheter, the tractor may extend within the catheter lumen. The tractor may connect to an inner puller that is typically coupled to an end of the tractor (which may be referred to as the inner end or the distal end) that can be pulled proximally to pull and invert the tractor over the distal end so that it rolls over the distal end, which may capture a clot. The apparatus may include a guidewire lumen extending through the catheter, tractor and/or tractor puller.

In general, a mechanical thrombectomy apparatus for removing a clot from a vessel may be a system, assembly or device including an elongate inversion support having a distal end and a distal annulus, and a flexible tractor assembly at least partially inverted and configured to roll and invert over the distal annulus of the elongate inversion support.

In many of the examples described herein, the elongate inversion support is a catheter (or a portion of a catheter at the distal end) and the annulus is formed by the distal end opening of the catheter; the tractor extends within the catheter and doubles back over the distal end of the catheter to extend over the outer diameter of the catheter at the distal end of the catheter, although it may extend proximal for any appropriate distance (including between 1-30 cm, between 2-20 cm, greater than 1 cm, 2 cm, 3 cm, 4 cm, 5 cm, 6 cm, 7 cm, 8 cm, 9 cm, 10 cm, 11 cm, 12 cm, 15 cm, 20 cm, etc.). The end of the tractor within the catheter may be coupled to a pusher (e.g., at a proximate pusher region connected to the distal or inner end of the tractor). The tubular tractor may include an elongate lumen that is configured to allow passage of a guidewire. The tubular tractor may also be configured to slide along the long axis within the catheter lumen and invert over the distal end opening of the catheter when the proximal end region is pulled proximally. The tractor may be referred to herein as a tractor assembly, tractor portion, tractor tube, or simply a tractor, and is typically positioned and longitudinally slideable within the catheter, and arranged so a portion of the tractor (sometimes referred to as the "distal tractor region" or "distal-facing" tractor region) doubles back over itself.

For example, FIG. 1A shows one variation of a catheter that may form part of the apparatuses described herein. In this example, the catheter 100 includes a distal end region 103 that includes a distal end 105. The distal end region may have an increasing softness (measured by durometer, e.g., shore durometer) except that the very distal tip (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

FIG. 1A shows one variation of a catheter of an elongate inversion support that may form part of the apparatuses described herein. In this example, the elongate inversion support includes a catheter 100 having a distal end region 103 that includes a distal end opening 105. The distal end region may have an increasing softness (measured by durometer, e.g., shore durometer) except that the very distalmost end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1A, the elongate inversion support is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of of compressive force is applied (e.g., at least about 700 g, 600 g, 500 g, 400 g, 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include a elongate inversion support that is not a full-length catheter, but may include a portion of a catheter, typically at the distal end, connected to a rod, wire, hypotube, or the like (as will be described in greater detail below in reference to FIGS. 7A-8D) or may be skived. Thus, any of the apparatuses and methods described herein may be adapted for use with an elongate inversion support that is not limited to catheters, including elongate inversion supports that include a portion of a catheter, or that include a ring or other structure forming the annulus at the distal end. In FIG. 1A the catheter 100 of the elongate inversion support may be any appropriate type of catheter or portion of a catheter, including microcatheters appropriate for neurovascular use.

In some variations the distal end 105 of the elongate inversion support is adapted so that the tractor may slide or roll and invert over the distal end of the catheter without being caught (binding, jamming) or without substantial friction. For example, in some variations the distal tip (end) may be curved or radiused 109 as shown in FIG. 1B, particularly on the outer surface (e.g., the transition from outer diameter to inner diameter).

FIG. 1C shows an example of a flexible tractor 144 coupled to a puller 146. In this example to form a pullable tractor assembly 140, the tractor is shown integrated with the puller, forming the assembly. In FIG. 1C, the tractor is a tube of material (e.g., wove, knitted, braided, etc.) that is flexible and elongate. The tractor is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less-expandable (or non-expandable) structure (tube, puller, etc.). In the example shown in FIG. 1C, the tractor 144 is configured, e.g., by shape-setting (heat setting, etc.), to expand in the relaxed first configuration to a radial diameter that is between 1.1 and 10 times the diameter of the inner diameter of the catheter of the elongate inversion support when unconstrained, as shown in FIG. 1D. In FIG. 1D, the tractor of FIG. 1C is shown in an expanded, relaxed, configuration. Thus the expandable tractor may be biased to expand open. The tractor may be formed of a mesh, braided, woven, knitted, or sheet of material and is generally adapted to grasp the object to be removed (e.g., blood clot).

In FIGS. 1C and 1D the tractor and puller have two portions, a tractor 144 and a less expandable (or non-expandable) proximal portion comprising the puller 146. The puller may be a separate region, such as a wire, catheter or hypotube, which is connected to an end region of the tractor (e.g., a flexible mesh, woven, braided, etc.), e.g., the distal end or near the distal end. The inverting region of the tractor, where it rolls and inverts over the distal end opening of the catheter may be referred to as the distal-facing region of the tractor, which may actively grab clot when rolling.

Figure 1E:
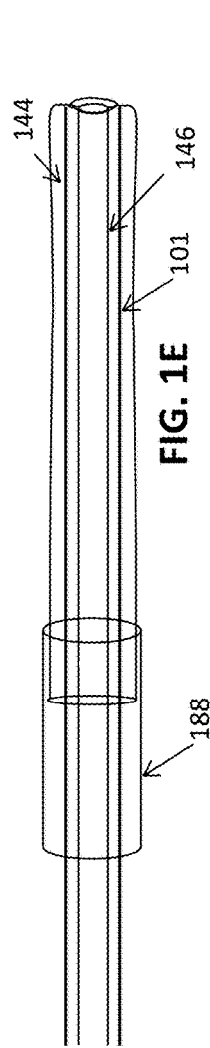
Figure 1F:
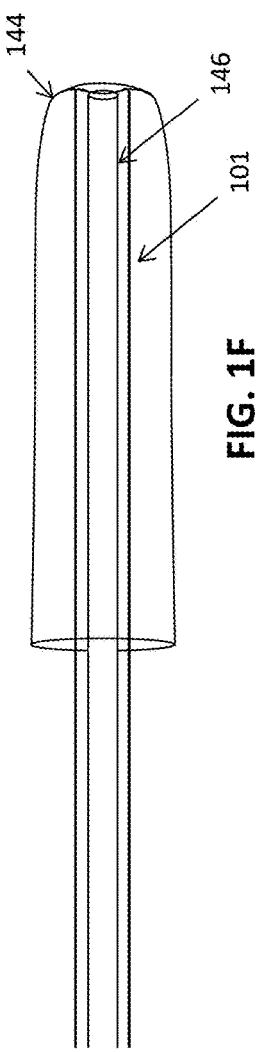

In FIG. 1E, the flexible tractor of FIG. 1C is shown with the tractor doubled back over itself an over the distal end of the catheter of the elongate inversion support 101. The distal end region is collapsed down, e.g., onto the puller and the elongate inversion support, and may be held collapsed. In this example a tractor hold 188 may be used to hold the tractor collapsed down onto the outer diameter of the elongate inversion support. However, in an unconstrained or deployed configuration, as shown in FIG. 1F, the tractor in this second configuration (e.g., the portion that is inverted over the distal end of the catheter) has an outer diameter that is greater than the outer diameter of the catheter of the elongate inversion support. Thus, the tractor 144 may be biased so that it has a relaxed expanded configuration in the first configuration (as shown in FIG. 1C) that is greater than the inner diameter (ID) of the catheter of the elongate inversion support portion of the apparatus and the relaxed expanded configuration of the second configuration (shown in FIG. 1F) inverted over the catheter has an OD that is greater than the OD of the catheter. The tractor is expandable and may be coupled to the puller. In some variations the flexible tractor and the puller may comprise the same material but the tractor may be more flexible and/or expandable, or may be connected to a push/pull wire or catheter.

Figure 1G:
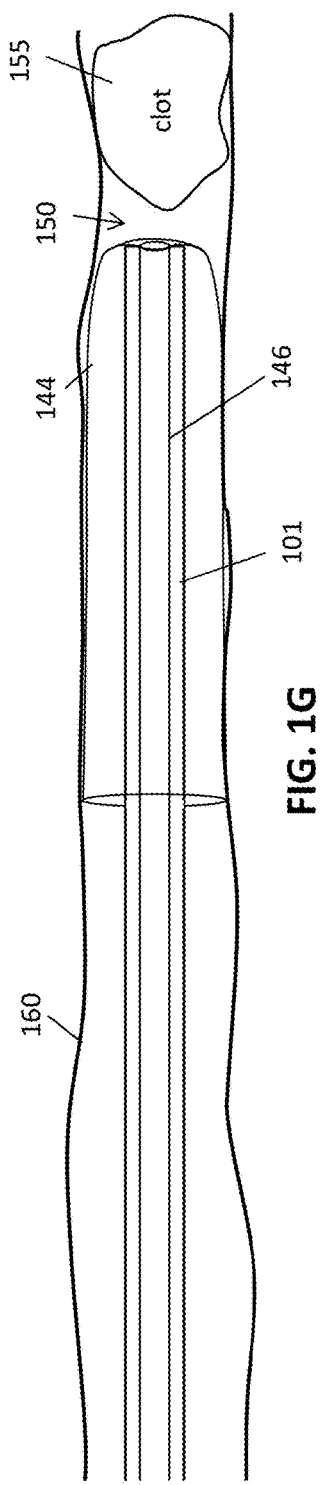
Figure 1H:
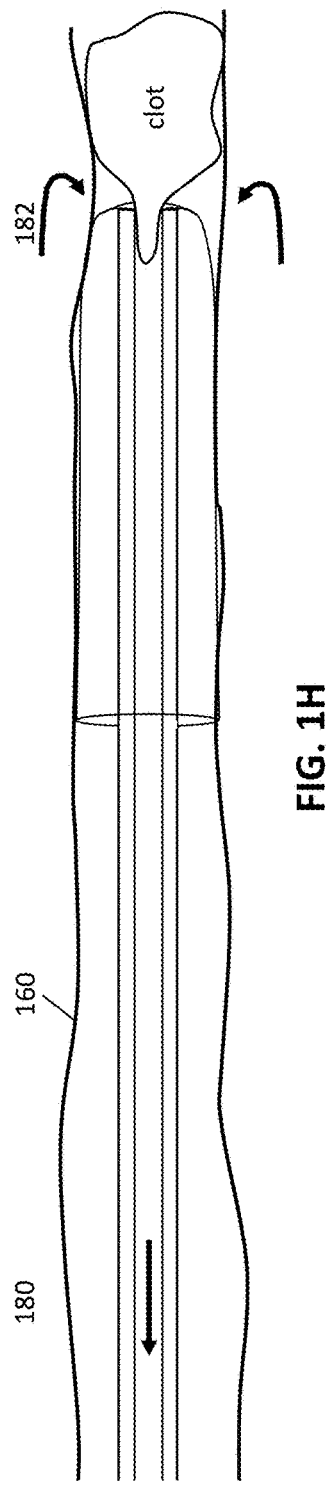

FIGS. 1G and 1H illustrate the removal of a clot using an apparatus such as the apparatus assembled from the components of FIGS. 1A and 1E. In this example the apparatus is configured as a thrombectomy apparatus including a catheter of an elongate inversion support 101 and a flexible tractor that extends over the distal end region of the catheter and doubles-over itself at the distal end of the catheter to invert so that the external tractor end region is continuous with an inner less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor. In FIG. 1G the apparatus is shown positioned and deployed within the vessel 160 near a clot 155. The clot may be drawn into the catheter by pulling the tractor 140 proximally into the catheter 101, as indicated by the arrow 180 showing pulling of the inner portion of the flexible tractor (e.g., using a handle, not shown) resulting in rolling the tractor over the end opening of the catheter and into the catheter distal end and inverting the expandable distal end region so that it is pulled into the catheter, shown by arrows 182. The end of the tractor outside of the catheter may be "loose" relative to the outer wall of the catheter. Another example of a tractor assembly includes a tractor that is coupled to a puller. The puller in this example is tapered (having tapering region)

and may therefore have a different flexibility of the distal end region than the proximal end region. For example the proximal end region may be less flexible than the narrower-diameter distal end region to which the tractor is coupled. The assembly includes a radiopaque marker. The tractor may be attached to the puller by any appropriate means. For example, the tractor may be crimped, glued, fused, or otherwise attached to the puller, typically permanently.

These apparatuses may be highly flexible, both before actuating and during operation. For example, in general, the flexible tractor may not increase the stiffness/flexibility of the catheter, and particularly the distal end region of the catheter too much, to avoid impacting maneuverability, particularly within tortious vessels of the neurovasculature. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm the catheter by less than 15% of the stiffness of the distal 5 cm of the catheter without the flexible tube extending therethrough and doubling back over the distal end of the catheter.

In any of the apparatuses described herein, in which the tractor is at least partially inverted over the distal end of the catheter so that the tractor extends on the outer surface of the catheter, the tractor may be releasably coupled to the outer diameter of the catheter to allow the apparatus to be inserted through a body, including through tortious vessels in the body, prior to being deployed to remove a clot or other element from the vessel. The tractor may be a braided, woven or knit material tube of material that is inverted over the distal end of the catheter; alternatively the tractor may be formed of a sheet of material that include openings therethrough.

Any of the apparatuses described herein may be adapted to prevent premature deployment of the tractor, e.g., by including a tractor hold (e.g., a housing, a lock, a clamp, etc.) or the like to secure the outer end of the tractor against and/or relative to the elongate inversion support. For example, a tractor hold may secure the outer end of the tractor against a catheter to which the tractor inverts when pulled proximally by the puller.

The tractor hold may compress the tractor against the catheter. Typically, the threshold force for the tractor hold is determined by the force required to deploy the tractor within the lumen, which may depend upon the length of the apparatus, the diameter of the tractor and/or catheter, and the materials of the tractor and elongate inversion support (e.g., catheter). For example, the tractor hold may be configured to hold the second end of the tractor until the threshold force is applied, wherein the threshold force is between 100 g force and 2000 g force (e.g., between 50 g of force and 2000 g of force, between 50 g of force and 1500 g of force, between 40 g of force and 1000 g of force, between 50 g of force and 500 g of force, between 100 g of force and 500 g of force, between 200 g of force and 500 g of force, between 250 g of force and 500 g of force, between 50 g of force and 450 g of force, between 100 g of force and 450 g of force, between 100 g of force and 400 g of force, between 200 g of force and 400 g of force, etc.). The range of force appropriate to the threshold force may be important in proper functioning of the apparatus, particularly when the force is applied by pulling proximally on the puller and/or tractor; too little force for the threshold and the tractor will prematurely deploy; too much force and the apparatus will jam (e.g., by kinking the elongate inversion support).

In any of the variations described herein, the tractor may be biased to collapse and/or expand. For example, the tractor may be biased to collapse over the catheter outer diameter (e.g., the outer diameter of the elongate inversion support, including the distal end of the catheter); such tractors may also be biased to expand after inverting (e.g., within the catheter) over the distal end opening of the elongate inversion support. This arrangement may cause the tractor to form a distal-facing region that flares, trumpet-like, towards a clot distal to the device, which may help in capturing the clot and also may prevent jamming of the tractor. Alternatively or additionally, some or all of the tractor regions may be configured to expand over the outer diameter of the elongate inversion support.

The proximal end of the tractor hold may be attached to the catheter. The tractor hold may be fixed, fused, or integrally formed with the catheter.

Any of the apparatuses described herein may be used to withdraw a clot and/or a clot engaging member. For example, FIGS. 2A-2G illustrate removal of a clot using a rolling thrombectomy apparatus. The apparatus may also be referred to as an inverting thrombectomy apparatus. In any of the variations described herein a vacuum may be used to help secure the clot to the tractor.

In FIG. 2A, the rolling mechanical thrombectomy apparatus 200 is brought near to the clot 220. In this example, a guidewire 205 may be used to help position the apparatus adjacent to the clot. The guidewire may be left in place or removed. Alternatively, as described in variations in which a clot engaging member on the distal end of an elongate manipulator is used, the apparatus 200 may be directed over the elongate manipulator. In FIG. 2A, the rolling thrombectomy apparatus includes a tractor 203 that is configured to roll over the distal end opening of a catheter 207. In FIG. 2A, the tractor is held in tension by holding in a fixed position relative to the catheter at a second (outer) end of the tractor; a tractor hold (not shown in FIG. 2A) may be used to releasably hold an end of the tractor fixed relative to the catheter. When a force sufficient to overcome the deployment force (e.g., 100 g of force or greater, 200 g of force or greater, etc.) is applied by pulling 219 the first end of the tractor, as shown in FIG. 2B. In FIG. 2B, the puller 209, coupled to the first end of the tractor within the catheter, is pulled to deploy the tractor. When deployed the tractor may expand away from the catheter and towards the wall(s) of the vessel 260.

As shown in FIG. 2B, the tractor may be rolled and inverted 282 into the catheter by pulling the first end of the tractor from within the catheter (e.g., by pulling 219 the puller proximally). The puller in FIGS. 2A-2G is shows as a hollow member (e.g., catheter, tube, etc.) but it may be a wire, cable, etc.

Occasionally, if the clot diameter is too large compared to the diameter of the distal end opening of the catheter, and/or if the clot is too stiff and difficult to compress, the clot 220 may jam in the distal end opening of the catheter after at least a portion of the clot has been grabbed by the tractor. This is illustrated in FIGS. 2B and 2C. In this example the force required to pull the clot into the catheter may be too high (e.g., greater than the longitudinal compression strength of the catheter, such as greater than 500 g of force, greater than 600 g of force, greater than 700 g of force, greater than 800 g of force, greater than 900 g of force, greater than 1000 g of force, greater than 1100 g of force, greater than 1200 g of force, greater than 1300 g of force, greater than 1400 g of force, greater than 1500 g of force, etc. the threshold may depend on the catheter type and structure.

When the clot is jammed within the catheter distal end opening, as shown in FIG. 2B (and in FIG. 3A), the method may then proceed to engulf and remove the clot with the tractor by withdrawing the catheter and continuing to pull the first end of the tractor proximally by pulling the puller proximally. In FIG. 2C, the catheter distal end opening 207' is shown withdrawn a substantial distance, e.g., beyond the second (outer) end of the tractor; alternatively the catheter may be withdrawn just slightly relatively to the tractor and/or may be withdrawn with the puller as the puller is withdrawn proximally.

As shown in FIG. 2D, when the puller is pulled proximally either with the catheter or with the catheter withdrawn proximally (as shown) so that the tractor cannot roll over the distal end opening of the tractor, the interference between the wall of the vessel 260 and the expanded tractor 251 may hold the tractor in place as the clot, which is still secured to the tractor either by the force of interaction between the tractor and the clot, and/or by suction (e.g., through the puller or other lumen connected to the tractor), is pulled proximally with the tractor. Thus, as shown in FIGS. 2D and 2E, the clot may be engulfed by the tractor and pulled proximally into the expanded tractor.

Ultimately, the tractor, clot and catheter may be removed proximally from the vessel. In some variations, as shown in FIGS. 2F and 2G, the clot may be pulled with the tractor into the catheter once it has been fully engulfed by the tractor. As illustrated in FIG. 3A, the clot may be jammed so that it is unable to be pulled into catheter by rolling the tractor so that it inverts into the catheter, similar to what was described above for FIG. 2B. In FIG. 3B, the clot has been pulled proximally with the tractor but not rolled over the catheter distal end opening; instead, the catheter has been withdrawn and the clot pulled into the tractor to invert itself round and engulf the clot within the tractor. Thus, pulling back the catheter proximally, even without pulling the tractor proximally or while pulling both the tractor and the catheter proximally, may drag the clot proximally and inert the tractor over the clot, as shown. As mentioned above, it may be helpful to have the tractor expand radially within the vessel to contact the wall of the vessel. This may help lock the tractor in position as the catheter and/or tractor is pulled proximally. The tractor may include at least a portion of its length that has an element that expands to the vessel wall. Inverting the tractor over the clot in this manner may reduce the risk of creating emboli compared to other techniques, including aspiration-only techniques, and also may not require the additional cost and risk of delivering a secondary device, such as a clot engaging member prior to or with the rolling mechanical thrombectomy apparatuses described herein (see below with regard to FIGS. 5A-7B for examples in which a clot engaging member is used in addition to the rolling mechanical thrombectomy apparatuses described herein.

Figure 4E:
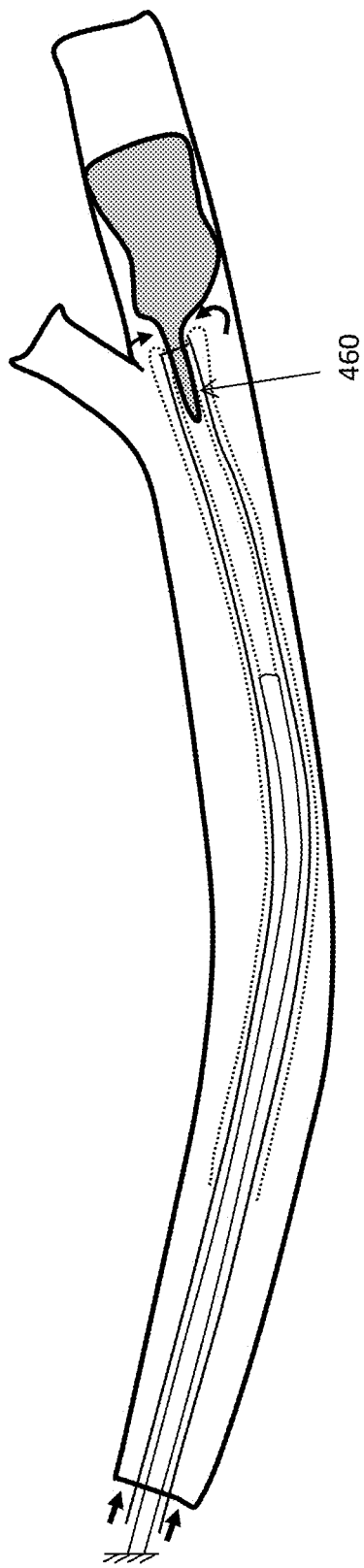

FIGS. 4A-4G illustrate another example of a method of capturing and/or removing a clot from a vessel using a rolling mechanical thrombectomy apparatus. In this example, rather than pulling the clot proximally into the tractor, the tractor (and catheter) may be advanced distally forward over the clot. For example, in FIG. 4A, a guide wire 405 (or other guide member) may be steered or driven distally to the clot 420. The guidewire may extend just to the clot or may pass at least partially though the clot. In some variations it may be beneficial to stop the guidewire prior to entering the clot, in order to avoid disrupting the clot. Once the guidewire is positioned, a rolling mechanical thrombectomy apparatus 400 may be positioned over the guidewire so that it is adjacent to the clot. The apparatus may include the catheter 401 and a tractor 403 that is coupled at a first end within the catheter to a puller (shown as a puller inner catheter 407). Optionally, the guidewire may be removed (as shown in FIG. 4C), leaving the rolling mechanical thrombectomy apparatus 400 behind.

Figure 4F:
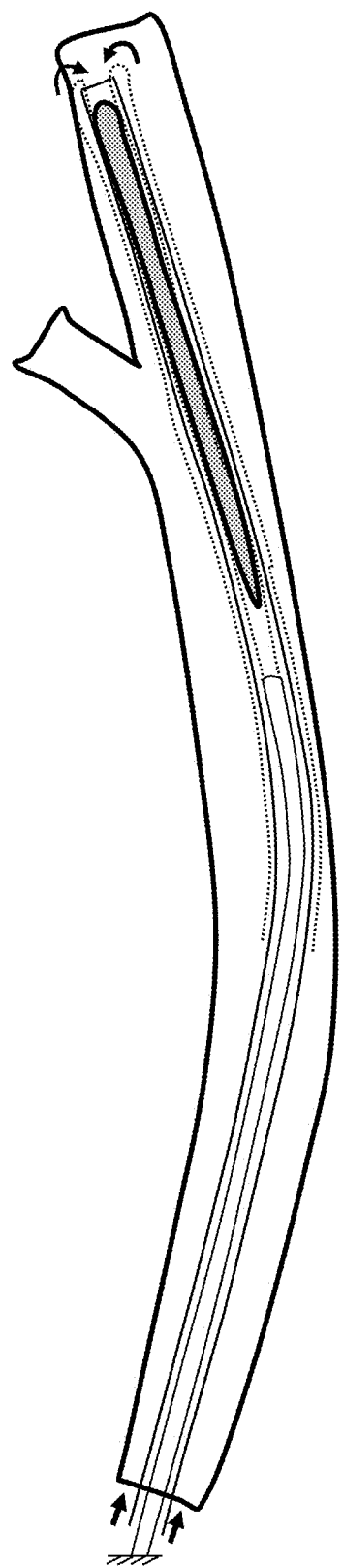
Figure 4G:
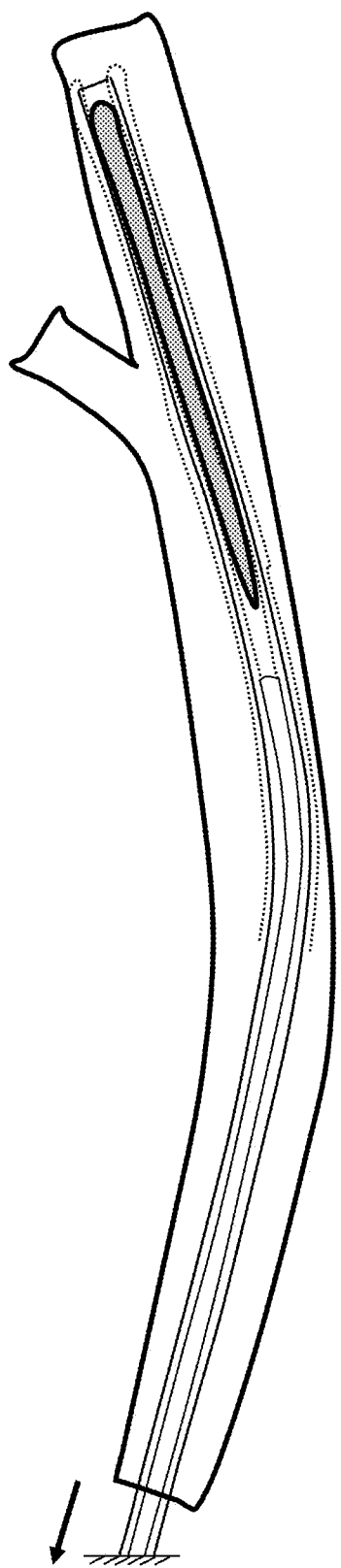

The tractor may then be rolled into the catheter and inverted by either pulling proximally on the puller (coupled within the catheter to the first end of the tractor), or alternatively and/or additionally by moving the catheter distally against the tractor, as shown in FIGS. 4C and 4D. In this example, the tractor puller is held in a relatively fixed position and the catheter is slowly advanced distally, towards the clot. The tractor therefore rolls and inverts 451 into the advancing catheter distal end, which may then travel up and into the clot 420, as shown in FIG. 4E. As the catheter advances, rolling the tractor so that it grabs and pulls the clot into the catheter distal end with the tractor, the tractor also envelops the clot and compresses it into the catheter inner lumen 460. Once the clot is engulfed and/or completely enveloped by the apparatus, the catheter forward (distal) motion may stop, as shown in FIG. 4F. Thereafter the catheter and tractor may be fixed in relative position (e.g., no motion relative to each other) and the apparatus slowly removed from out of the vessel, as shown in FIG. 4G, with the clot within the tractor and the tractor and clot within the lumen of the catheter.

As mentioned above, any of the methods and apparatuses described herein may be used with (and/or may integrate into them) a clot engaging member on the distal end of an elongate manipulator. Any type of clot engaging member may be used, and particularly those on on the distal end of an elongate manipulator. For example, FIGS. 5A-5C illustrate different schematic variations of clot engaging member on the distal end of an elongate manipulator. In FIG. 5A the clot engaging member 501 is a coil that is on the distal end of an elongate manipulator 503. The coil may be expandable, e.g., may be compressed so that when released at or near the clot it may expand. The clot engaging member may be secured into the clot or through the clot so that, once expanded, it may help mechanically capture the clot.

FIG. 5B shows another example of a clot engaging member 501' on the distal end of an elongate manipulator 503'. In FIG. 5B, the clot engaging member includes a plurality of wires that may expand outward within the clot. Similarly, FIG. 5C illustrates another example of a clot engaging member 501" on the distal end of an elongate manipulator 503".

Any of the apparatuses described herein may be used in conjunction with a clot engaging member, and particularly a clot engaging member on the distal end of an elongate manipulator.

FIG. 6I illustrates an example of a mechanical thrombectomy system for removing a clot from within a vessel. In FIG. 6I, the apparatus (e.g., system) includes an elongate inversion support comprising a catheter 607 having a distal end and a distal end opening, a tractor 615 comprising a flexible tube that extends distally in an un-inverted configuration within the catheter, inverts over the distal end opening of the catheter and extends proximally in an inverted configuration along the distal end of the catheter, wherein the tractor is configured to invert by rolling over the distal end opening of the catheter when a first end of the tractor is pulled proximally within the catheter. The system also includes a puller 611 connected to the first end of the tractor that extends proximally within the catheter. The system also includes a clot engaging member 601 on the distal end of an elongate manipulator 603. The elongate member is shown passing through a lumen extending continuously through the puller and the tractor and configured to pass the expandable elongate manipulator. This system may be used to remove a clot.

For example, a clot engaging member on the distal end of an elongate manipulator may be advanced through a clot; the expansive/expandable clot engaging member on the distal end of the elongate manipulator may engage with a clot and lock the clot in place in the vessel. The rolling mechanical thrombectomy apparatus may then be delivered, e.g., over the elongate manipulator to the clot and the clot engaging member. Once near the clot, the tractor may be rolled into the distal end of the catheter by pulling the first end of the tractor (e.g., by pulling a puller) proximally and advancing the catheter distally and/or by holding the puller in a relatively fixe position and driving the catheter distally to roll the tractor and invert it into the catheter. Preferably, as illustrated in FIGS. 4A-4G above, the catheter may be advanced forward in the vessel and the proximal end of the tractor may be held and/or fixed (in a fixed longitudinal position). For example, the proximal end of the tractor may be a puller/catheter that is slid over the elongate manipulator and, once positioned adjacent to the clot, held in a fixed position relative to the elongate manipulator. Holding the proximal puller fixed to the elongate manipulator while advancing the catheter forward distally relative to the elongate manipulator may therefore invert the tractor over the clot and clot engaging member similar. This action may force the tractor to roll into the distal end opening of the catheter and grab and engulf the clot along with the clot engaging member. In this example, the clot engaging member may be in the clot and/or distal to the clot, and the elongate manipulator acts as a guide rail for the rolling mechanical thrombectomy apparatus as the catheter is advanced forward. This example is illustrated in FIGS. 6A-6I.

For example, in FIG. 6A, the clot engaging member 601 on the distal end of an elongate manipulator 603 is advanced distally into and through the clot 620. Thus, the clot engaging member engages the clot from the distal side of the clot, and may pull against the clot when drawn proximally. Alternatively, FIG. 6B shows an example in which the engaging member 601 on the distal end of an elongate manipulator 603 is deployed within the clot 620. The engaging member may engage the clot by expanding within the clot.

Figure 6F:
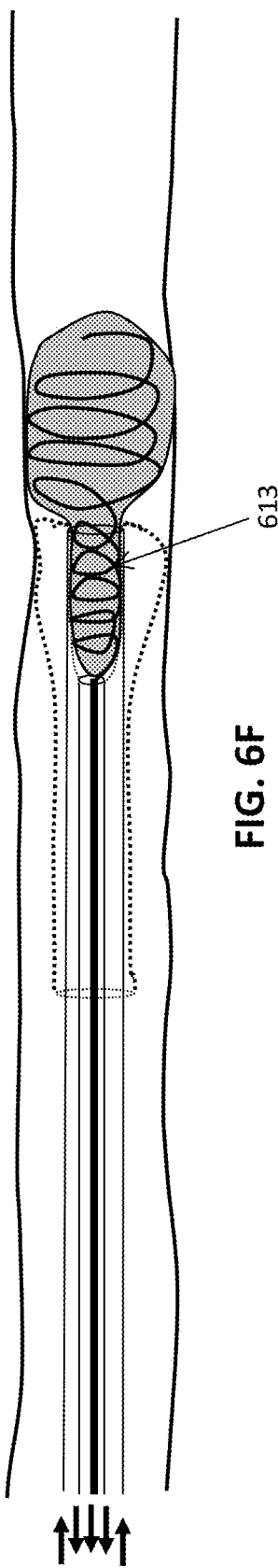
Figure 6G:
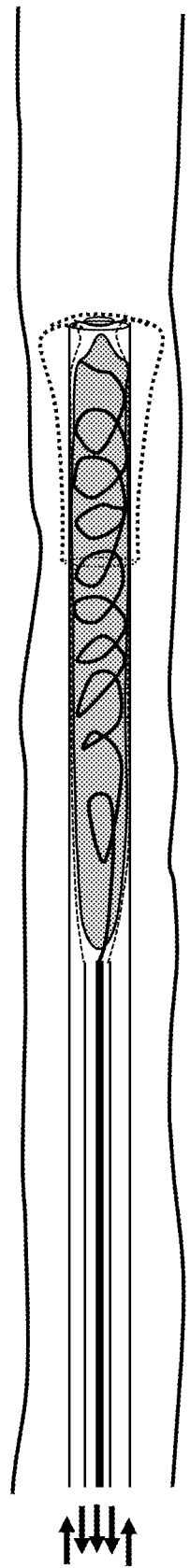
Figure 6H:
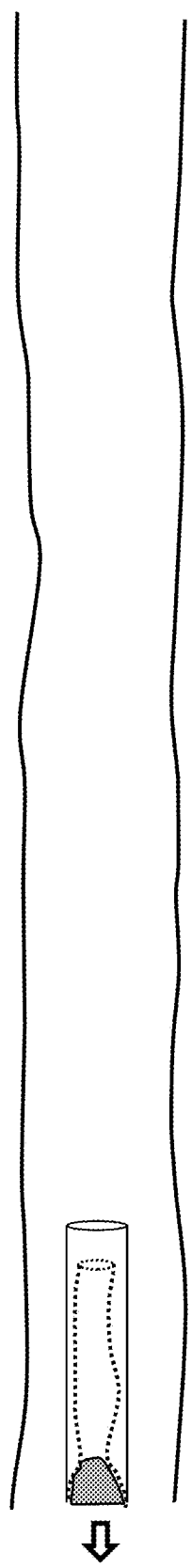
Figure 61:
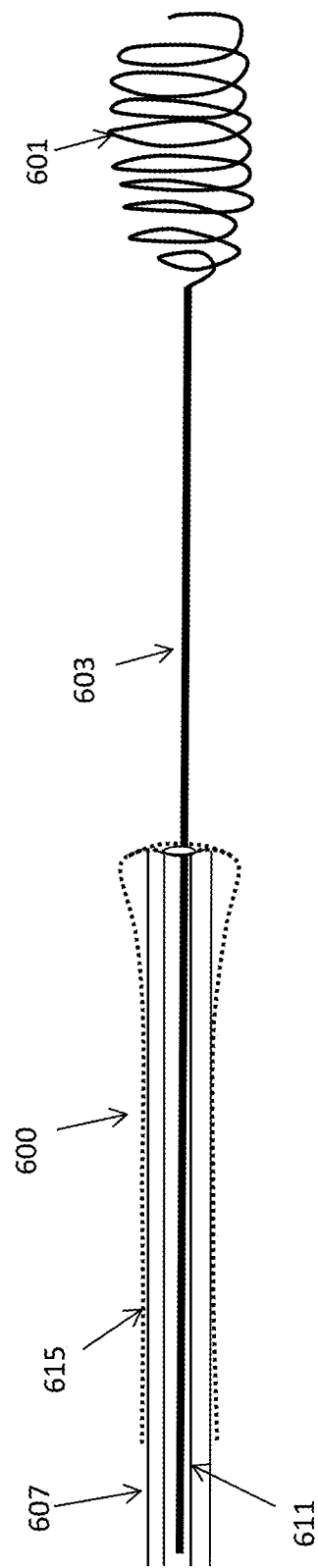

Once deployed, the engaging member and clot may be captured by a rolling mechanical thrombectomy apparatus, as shown in FIG. 6C. Once adjacent to the clot, the apparatus may be advanced distally by driving the catheter 607 distally 609, as shown in FIG. 6D. The elongate manipulator 603 and the puller 611 coupled to the first end of the tractor may be held fixed relative to one another (and/or may be jointly pulled proximally) while the catheter 607 is pushed distally 609, as shown in FIG. 6E. This may therefore roll the tractor over the distal end of the catheter and capture the clot and clot engaging member, pulling it into the catheter 613 as shown in FIG. 6F. This process may be continued until the entire clot and clot engaging member is engulfed and held within the catheter, as shown in FIG. 6G. Once complete, the apparatus, clot and clot engagement member may be withdrawn proximally out of the vessel, as shown in FIG. 6H.

Alternatively, a clot engagement member may be deployed through a rolling mechanical thrombosis apparatus in order the engage with the clot before removing with the rolling mechanical thrombosis apparatus.

In any of the variations described herein, the tractor may be actuated by advancing the catheter portion distally over the clot and clot engagement member either with or without pulling the tractor (e.g., puller) proximally within the catheter. The tractor may grab the clot and clot engagement member and may be advanced forward distally over both the clot and the clot engagement mechanism. This technique may avoid dragging the clot engagement apparatus within the vessel and may provide active capturing. This may reduce the risk of any distal emboli on embolization of new territories. As mentioned above, in any of these variations suction/aspiration can be used in combination with any of these steps.

In any of these variations, the clot engaging mechanism may be pulled proximally into the pre-loaded dozer catheter, rather than advancing the apparatus over the clot engaging mechanism; as the clot engagement mechanism pulls into the pre-loaded tractor and catheter, the tractor may grab and encapsulate the clot as the clot and clot engagement mechanism is pulled proximally.

FIGS. 7A and 7B illustrate an example in which the clot engagement apparatus 703 is linked to the puller 705, so that the two may be moved or held motionless together, relative to the catheter 707, and/or the vessel. For example, in FIG. 7B, the apparatus is inserted into the vessel and adjacent to clot engagement mechanism and held motionless while the catheter is driven forward, allowing the tractor 713 to roll distally and into the catheter and and capture the clot without requiring the clot and/or clot engagement mechanism to move within the vessel. This may reduce the risk for further embolization.

As mentioned above, any of the apparatuses and methods described herein may be used with aspiration (e.g., vacuum). For example, any of these methods described herein may may use a combination of aspiration and a tractor pull mechanism. For example, to initiate the grabbing of the clot by the tractor, the tractor may be rolled around a catheter wall and may make physical (e.g., direct) contact with the clot. A user may apply vacuum through the catheter (e.g., via a syringe or pump, etc.) prior to or at the same time as pulling tractor into the catheter. Alternatively or additionally, vacuum may be applied through the puller (e.g., a pulling catheter). If vacuum is applied prior to pulling the tractor the vacuum may be applied 1 sec to 5 min prior ensure the clot is in good contact with the distal end of the catheter. Preferred range of 5-60 sec vacuum prior to activating/pulling dozer. The application of vacuum prior to pulling the braid will ensure the proximal most end of the clot is in contact with the catheter tip and some amount of the clot (>0.5 mm) is extruded into the lumen of the catheter tip. Next when the dozer is pulled there will be clot at the tip of the catheter for the braid/dozer to grab and pull in. Also, when the dozer is pulled there are resultant forces from the braid/dozer that put compression forces on the catheter tip encouraging the catheter tip to buckle and/or move proximally away from the proximal edge of the clot. The application of vacuum ensures that even if the catheter tip wants to move proximally when pulling the tractor that the clot will stay in contact with the clot and/or prevent the catheter tip from pulling back away from the clot. Once the tractor engages a grabs a few mm of clot the vacuum may be kept on or turned off.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of removing a clot from within a vessel using a mechanical thrombectomy apparatus, the method comprising:
    positioning a distal end of the mechanical thrombectomy apparatus adjacent to the clot within the vessel, wherein the mechanical thrombectomy apparatus includes a tractor region that extends along a distal region of a catheter and inverts over a distal end of the catheter so that a first end of the tractor extends proximally within the catheter;
    pulling the first end of the tractor proximally within the catheter to roll the tractor over the distal end of the catheter so that the tractor inverts over the distal end of the catheter and pulls the clot into the catheter with the inverting tractor;
    withdrawing the catheter proximally away from the tractor and clot when the tractor jams on the distal end of the catheter;
    pulling the first end of the tractor proximally so that the tractor inverts over the clot within the vessel without rolling over the distal end opening of the catheter; and
    withdrawing the tractor and clot proximally from the vessel.

2. The method of claim 1, further comprising disengaging a second end of the tractor from a tractor hold that secures the second end of the tractor to an outer surface of the catheter by pulling the tractor proximally with a force greater than a deployment force and expanding the tractor against the vessel wall, wherein the second end of the tractor is disengaged before pulling the first end of the tractor proximally.

3. The method of claim 1, further comprising pulling proximally on the tractor to draw the tractor and clot into the catheter.

4. The method of claim 1, wherein pulling the first end of the tractor proximally within the catheter to roll the tractor over the distal end of the catheter comprises advancing the catheter while pulling the first end of the tractor.

5. The method of claim 1, wherein pulling the first end of the tractor proximally so that the tractor inverts over the clot further comprises pulling the catheter proximally with the first end of the tractor.

6. The method of claim 1, wherein pulling the first end of the tractor proximally so that the tractor inverts over the clot comprises pulling a puller at the proximal end of the mechanical thrombectomy apparatus proximally.

7. The method of claim 1, wherein pulling the first end of the tractor proximally within the catheter to roll the tractor over the distal end of the catheter comprises engaging the clot with the tractor.

8. The method of claim 1, wherein withdrawing the catheter proximally away from the tractor comprises pulling the catheter proximally beyond a second end of the tractor that is outside of the catheter.

9. The method of claim 1, wherein pulling the first end of the tractor proximally so that the tractor inverts over the clot comprises pulling the first end of the tractor when the tractor has expanded to contact the vessel wall.

10. The method of claim 1, further wherein positioning the distal end of the mechanical thrombectomy apparatus adjacent to the clot comprises sliding the mechanical thrombectomy apparatus over a guidewire or catheter passing through a lumen in the mechanical thrombectomy apparatus.

11. A method of removing a clot from within a vessel using a mechanical thrombectomy apparatus, the method comprising:
    positioning a distal end of the mechanical thrombectomy apparatus adjacent to the clot within the vessel, wherein the mechanical thrombectomy apparatus includes a tractor region that extends along a distal region of a catheter and inverts over a distal end of the catheter so that a first end of the tractor extends proximally within the catheter;
    disengaging a second end of the tractor from a tractor hold that secures the second end of the tractor to an outer surface of the catheter by pulling the tractor proximally with a force greater than a deployment force and expanding the tractor against the vessel wall;
    pulling the first end of the tractor proximally within the catheter to roll the tractor over the distal end of the catheter so that the tractor inverts over the distal end of the catheter and pulls the clot into the catheter with the inverting tractor;
    withdrawing the catheter proximally away from the tractor and clot when the tractor jams on the distal end of the catheter;
    pulling the tractor and clot proximally so that the tractor inverts over the clot within the vessel without rolling over the distal end opening of the catheter;
    pulling proximally on the tractor to draw the tractor and clot into the catheter; and
    withdrawing the tractor and clot proximally from the vessel.

12. The method of claim 11, wherein pulling the first end of the tractor proximally within the catheter to roll the tractor over the distal end of the catheter comprises advancing the catheter while pulling the first end of the tractor.

13. The method of claim 11, wherein pulling the first end of the tractor proximally so that the tractor inverts over the clot further comprises pulling the catheter proximally with the first end of the tractor.

14. The method of claim 11, wherein pulling the first end of the tractor proximally so that the tractor inverts over the clot comprises pulling a puller at the proximal end of the mechanical thrombectomy apparatus proximally.

15. The method of claim 11, wherein withdrawing the catheter proximally away from the tractor comprises pulling the catheter proximally beyond a second end of the tractor that is outside of the catheter.

16. The method of claim 11, wherein pulling the first end of the tractor proximally so that the tractor inverts over the clot comprises pulling the first end of the tractor when the tractor has expanded to contact the vessel wall.

17. The method of claim 11, further wherein positioning the distal end of the mechanical thrombectomy apparatus adjacent to the clot comprises sliding the mechanical thrombectomy apparatus over a guidewire or catheter passing through a lumen in the mechanical thrombectomy apparatus.

* * * * *